US011288576B2

(12) United States Patent
Dutta et al.

(10) Patent No.: US 11,288,576 B2
(45) Date of Patent: Mar. 29, 2022

(54) PREDICTING QUALITY OF SEQUENCING RESULTS USING DEEP NEURAL NETWORKS

(71) Applicant: Illumina, Inc., San Diego, CA (US)

(72) Inventors: Anindita Dutta, San Diego, CA (US); Amirali Kia, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 975 days.

(21) Appl. No.: 15/863,790

(22) Filed: Jan. 5, 2018

(65) Prior Publication Data

US 2019/0213473 A1    Jul. 11, 2019

(51) Int. Cl.
| | |
|---|---|
| G06N 3/08 | (2006.01) |
| G16B 30/00 | (2019.01) |
| G16B 40/10 | (2019.01) |
| C12Q 1/6869 | (2018.01) |
| G06N 5/02 | (2006.01) |

(52) U.S. Cl.
CPC ............. G06N 3/08 (2013.01); C12Q 1/6869 (2013.01); G06N 5/022 (2013.01); G16B 30/00 (2019.02); G16B 40/10 (2019.02)

(58) Field of Classification Search
CPC .......... G06N 3/08; G06N 5/022; G16B 40/10; G16B 30/00; C12Q 1/6869
See application file for complete search history.

(56) References Cited

U.S. PATENT DOCUMENTS

| | | | |
|---|---|---|---|
| 4,903,192 A | 2/1990 | Saito | |
| 5,365,455 A | 11/1994 | Tibbetts et al. | |

(Continued)

FOREIGN PATENT DOCUMENTS

| | | |
|---|---|---|
| CA | 2928209 A1 | 6/2015 |
| CN | 101339434 A | 1/2009 |

(Continued)

OTHER PUBLICATIONS

Sequencing Analysis Viewer v1.11 Software Guide from https://studylib.net/doc/18628005/sequencing-analysis-viewer-software-guide—support (Year: 2016).*

(Continued)

*Primary Examiner* — Alexey Shmatov
*Assistant Examiner* — Hamza R Mughal
(74) *Attorney, Agent, or Firm* — Haynes Beffel & Wolfeld, LLP; Ernest J. Beffel, Jr.; Sikander M. Khan

(57) ABSTRACT

The technology disclosed predicts quality of base calling during an extended optical base calling process. The base calling process includes pre-prediction base calling process cycles and at least two times as many post-prediction base calling process cycles as pre-prediction cycles. A plurality of time series from the pre-prediction base calling process cycles is given as input to a trained convolutional neural network. The convolutional neural network determines from the pre-prediction base calling process cycles, a likely overall base calling quality expected after post-prediction base calling process cycles. When the base calling process includes a sequence of paired reads, the overall base calling quality time series of the first read is also given as an additional input to the convolutional neural network to determine the likely overall base calling quality after post-prediction cycles of the second read.

20 Claims, 10 Drawing Sheets

(56) References Cited

U.S. PATENT DOCUMENTS

| | | | |
|---|---|---|---|
| 5,548,252 | A | 8/1996 | Watanabe et al. |
| 6,951,998 | B2 | 10/2005 | Mammp et al. |
| 7,669,777 | B2 | 3/2010 | Hull |
| 8,392,126 | B2 | 3/2013 | Mann et al. |
| 8,965,076 | B2 | 2/2015 | Garcia et al. |
| 9,444,880 | B2 | 9/2016 | Dickinson et al. |
| 2008/0088857 | A1 | 4/2008 | Zimmer et al. |
| 2010/0157086 | A1 | 6/2010 | Segale et al. |
| 2011/0256631 | A1* | 10/2011 | Tomaney ............ C12Q 1/6874 436/94 |
| 2012/0173159 | A1* | 7/2012 | Davey ............... G01N 27/4145 702/20 |
| 2013/0090860 | A1* | 4/2013 | Sikora .................. G16B 25/00 702/20 |
| 2014/0214579 | A1 | 7/2014 | Shen et al. |
| 2014/0316716 | A1* | 10/2014 | Jiang ..................... G16B 30/00 702/20 |
| 2015/0125053 | A1 | 5/2015 | Vieceli |
| 2015/0169824 | A1* | 6/2015 | Kermani ............... G16B 40/00 702/19 |
| 2015/0243028 | A1* | 8/2015 | Garcia .................. G06T 7/0012 382/129 |
| 2016/0026757 | A1* | 1/2016 | Li ......................... G16B 40/00 702/19 |
| 2017/0349874 | A1 | 12/2017 | Jaques et al. |
| 2018/0195953 | A1 | 7/2018 | Langlois et al. |
| 2018/0274023 | A1 | 9/2018 | Belitz |

FOREIGN PATENT DOCUMENTS

| | | |
|---|---|---|
| CN | 104566863 A | 4/2015 |
| CN | 104822842 A | 8/2015 |
| CN | 105420096 A | 3/2016 |
| JP | 2004501415 A | 1/2004 |
| JP | 2013248860 A | 12/2013 |
| JP | 5488140 B2 | 5/2014 |
| JP | 5604945 B2 | 10/2014 |
| WO | 2011127386 A2 | 10/2011 |
| WO | 2013082619 A1 | 6/2013 |
| WO | 2015084985 A2 | 6/2015 |
| WO | 2015190249 A1 | 12/2015 |
| WO | 2016065299 A2 | 4/2016 |
| WO | 2018165099 A1 | 9/2018 |

OTHER PUBLICATIONS

"Phasing and Prephasing FAQ", Scientific Knowledge Base, Nov. 29, 2017, 1-20.

Hedegaard, J., "An introduction to "Next Generation" DNA Sequencing", AARHUS Universitet http://staff.vbi.vt.edu/mlawre04/NextGen%20Genomics%20Class/Technology%20-%20Module_6_NGS_intro.pdf, 2010, 1-63.

Illumina, "Illumina Two-Channel SBS Sequencing Technology", https://www.illumina.com/science/technology/next-generation-sequencing/sequencing-technology/2-channel-sbs.html, Jan. 4, 2016, 1-2.

Illumina, "Low-Diversity Sequencing on the Illumina HiSeq Platform", https://www.illumina.com/documents/products/technotes/technote-hiseq-low-diversity pdf, Aug. 20, 2014, 1-2.

Illumina, "Quality Scores for Next-Generation Sequencing", https://www.illumina.com/documents/products/technotes/technote_Q-Scores pdf, 2011, 1-2.

Illumina, "Reducing Whole-Genome Data Storage Footprint", http://www.illumina.com/documents/products/whitepapers/whitepaper_datacompression.pdf, Apr. 17, 2014, 1-4.

Illumina, "Sequencing Analysis Viewer Software User Guide", https://support.illumina.com/downloads/sequencing-analysis-viewer-software.html, Oct. 17, 2014, 1/33.

Ioffe, S., et al., "Batch Normalization: Accelerating Deep Network Training by Reducing Internal Covariate Shift", arXiv:1502.03167 [cs.LG], Feb. 11, 2015.

Leshkowitz, D., "Illumina Primary Analysis Pipeline and Quality Control", Weizmann Institute of Science, 2016, 1-48.

Townley, D., "Illumina Primary and Secondary Analysis", https://www.illumina.com/documents/seminars/presentations/2010-06_sq_04_townley_ngs_analysis.pdf, Jun. 2010, 1-33.

PCT/US2019/012398—International Search Report and Written Opinion dated May 9, 2019, 18 pages.

Ilumina: "Genome Analyzer IIX User Guide (for SCS v2.10)," Jun. 27, 2012, pp. 1-198.

PCT/US2019/012216—International Search Report and Written Opinion dated May 22, 2019, 25 pages.

McCarthy et al., "A Comparison of Methods to Interpret the Basal Body Temperature Graph Supported in Party By Funds from the National Institute of Child Health and Human Development and the Office for Family Planning," Fertility and Sterility, vol. 39, No. 5, May 1, 1983, pp. 640-646.

PCT/US2019/012398—International Preliminary Report on Patentability dated Jan. 3, 2020, 19 pages.

PCT/US2019/012398—Article 34 Amendments dated Nov. 5, 2019, 23 pages.

AU 2019205311—Voluntary Amendments filed Apr. 24, 2020, 24 pages.

EP 19705419.0—Voluntary Amendments filed Jul. 20, 2020, 9 pages.

AU 2019205311—First Office Action dated Jun. 10, 2020, 5 pages.

SG 11201911754T—Voluntary Amendments filed Aug. 18, 2020, 12 pages.

EP 19705419.0—Communication under Rule 71(3) dated Jan. 22, 2021, 39 pages.

Pacific Biosciences Develops Transformative DNA Sequencing Technology, Pacific Biosciences Technology Backgrounder, Nov. 24, 2008, 14 pages.

Chen et al., High-throughput platform for real-time monitoring of biological processes by multicolor single-molecule fluorescence, Proceedings of the National Academy of Sciense of USA (PNAS), Jan. 4, 2014, vol. 11, No. 2, 6 pages (www.pnas.org/cgi/doi/10.1073/pnas.1315735111).

Dhillon, Balbir S. Engineering maintenance: a modern approach. cRc press, 2002, 222 pages.

Hoppenstedt et al., "Techniques and Emerging Trends for State of the Art Equipment Maintenance Systems—A Bibliometric Analysis." Applied Sciences 8, No. 6 (2018): 29 pages.

Illumina, BaySpace Onsite v2.1 HT, System Guide, Oct. 2015, 78 pages.

Illumina, BaySpace Sequence Hub, Jun. 26, 2016, 4 pages.

Illumina, "Illumina Proactive Technical Note," 2018, 12 pages.

Illumina, Software, HCS FAQ Sequencig Instruments, accessed Nov. 21, 2018, 1 page.

Kothamasu et al., "System health monitoring and prognostics—a review of current paradigms and practices." The International Journal of Advanced Manufacturing Technology 28, No. 9-10 (2006): 1012-1024.

Niu et al., "Development of an optimized condition-based maintenance system by data fusion and reliability-centered maintenance." Reliability Engineering & System Safety 95, No. 7 (2010): 786-796.

Shmueli et al., "Predictive analytics in information systems research." MIS quarterly (2011): 553-572.

PCT/US2019/012216—Article 34 Amendments dated Nov. 5, 2019, 10 pages.

CN 201980003254X—Voluntary Amendments filed May 18, 2020, 22 pages.

AU 2019205267—First Office Action dated Jun. 11, 2020, 4 pages.

U.S. Appl. No. 16/239,342—Notice of Allowance dated Aug. 19, 2020, 17 pages.

AU 2019205267—Second Office Action dated Jan. 19, 2021, 3 pages.

CN 201980003254X—First Office Action dated Sep. 7, 2020, 20 pages with English translation.

CN 201980003254X—Response to First Office Action dated Sep. 7, 2020, filed Jan. 20, 2021, 6 pages.

EP 19705412.5—Response to rule 161(1) & 162 dated Feb. 12, 2020, filed on Aug. 21, 2020, 18 pages.

(56) References Cited

OTHER PUBLICATIONS

EP 19705412.5—Rule 161(1) & 162 communication dated Feb. 12, 2020, 3 pages.
JP 2019-567671 First Office Action, dated Feb. 8, 2021, 6 pages.
KR 10-2019-7036281 First Office Action, dated Aug. 10, 2020, 3 pages.
KR 10-2019-7036281 Response to First Office Action, dated Oct. 7, 2020, 6 pages.
KR 10-2019-7036281 Notice of Allowance, dated Nov. 16, 2020, 3 pages.
SG 11201911754T Voluntary Amendments, dated Aug. 18, 2020, 12 pages.
NZ 759639 First Office Action, dated Jun. 9, 2021, 4 pages.
JP 2019-567671 Response to First Office Action dated Feb. 8, 2021, filed May 10, 2021, 8 pages.
AU 2019205311—Response to First Office Action dated Jun. 10, 2020, filed Jul. 20, 2021, 56 pages.
AU 2019205311—Notice of Allowance, dated Aug. 13, 2021, 3 pages.
EP 19705419.0 Decision to Grant, dated Jun. 10, 2021, 2 pages.
JP 2019-567671 Notice of Allowance, dated Oct. 18, 2021, 8 pages.
Lopopolo et al., Sequencing Quality Control, Oxford Genomics Centre, dated Jul. 6, 2017, 6 pages. Retrieved on Jul. 6, 2017. Retrieved from the internet [URL: https://www.well.ox.ac.uk/ogc/sequencing-quality-monitoring-run/ ].
PCT/US2019/012216—International Report on Patentability dated Jan. 8, 2020, 29 pages.
AU 2019205267 Response to Second Office Action, response dated Apr. 16, 2021, 147 pages.
CA 3065862 First Office Action, dated Feb. 25, 2021, 4 pages.
CN 201980003254X Second Office Action, dated Mar. 18, 2021, 24 pages.
EP 19705412.5 First Office Action, dated Feb. 25, 2021, 3 pages.
KR 10-2019-7038075 Response to First Office Action dated Feb. 25, 2021, filed Apr. 26, 2021, 23 pages.
JP 2019-567589 First Office Action, dated Jan. 25, 2021, 9 pages.
JP 2019-567589 Response to First Office Action, filed Apr. 26, 2021, 8 pages.
KR 10-2019-7038075 First Office Action, dated Feb. 25, 2021, 5 pages.
AU 2019205267 Notice of Acceptance, dated May 12, 2021, 3 pages.
NZ 759644 First Office Action, dated Jun. 4, 2021, 3 pages.
CN 201980003254X Response to Second Office Action, filed May 25, 2021, 20 pages.
CN 201980003254X Notice of Allowance, dated Jul. 6, 2021, 4 pages.
CA 3065862 Response to First Office Action dated Feb. 25, 2021, filed Jun. 24, 2021, 8 pages.
EP 19705412.5 Response to First Office Action dated Feb. 25, 2021, filed Jun. 30, 2021, 61 pages.
JP 2019-567589 Notice of Allowance, dated Sep. 13, 2021, 6 pages.
KR 10-2019-7038075 Notice of Allowance, dated Aug. 5, 2021, 3 pages.
IL 282262 Response to Notice Before Examination dated Apr. 18, 2021, filed Jul. 25, 2021, 144 pages.

* cited by examiner

Data from Sequencing Systems

500

| Chemical Processing Subsystem Performance Data 116 | Image Registration Subsystem Performance Data 117 | Image Acquisition Subsystem Performance Data 118 | Overall Base Calling Quality Data 119 |
|---|---|---|---|
| Phasing<br>Prephasing | Translation X<br>Translation Y | Intensity<br>Maximum Contrast<br>Minimum Contrast<br>Focus Score | %Q>30 |

Cycle 1:  97.60352     3.017356     2.989338     98.29049917
         97.13831                  3.06155

• • •

Cycle 25: 95.62704    3.017356     2.865425     96.90144042
          95.55764                  3.162942

FIG. 5

PREDICTING QUALITY OF SEQUENCING RESULTS USING DEEP NEURAL NETWORKS

FIELD OF THE TECHNOLOGY DISCLOSED

The technology disclosed relates to artificial intelligence type computers and digital data processing systems and corresponding data processing methods and products for emulation of intelligence, including machine learning systems and artificial neural networks. In particular, the technology disclosed relates to using deep learning and deep convolutional neural networks for analyzing ordered data.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Various protocols in biological or chemical research involve performing a large number of controlled reaction cycles. Some DNA sequencing protocols such as sequencing-by-synthesis (SBS) detect light emissions from an array of reaction sites. In SBS, a plurality of fluorescently-labeled nucleotides are used to sequence nucleic acids of numerous clusters (or clonal populations) of amplified DNA that are located on the surface of a substrate. The surface may, for example, define a channel in a flow cell. The sequences of the nucleic acids in the different clusters are determined by running hundreds of cycles in which a fluorescently-labeled nucleotide is added to the cluster and then excited by a light source to provide light emissions.

Although SBS is an effective technique for determining a sequence of the nucleic acids, an SBS run can take three days or more to complete. Some runs fail, due to quality problems. Reliably predicting the final quality of a sequencing run after a handful of cycles would benefit users of sequencing instruments, by allowing them to halt a bad run after half a day or less. Operators of sequencing instruments cannot predict the final quality of a sequencing run early along.

Fortunately, large sets of subsystem performance data are available that have been collected for performing trouble shooting. This subsystem data can be combined and used to predict the overall base calling quality at the end of a sequencing read or run and at intervals during a read. Using the subsystem performance metrics reported early in a run, a trained deep neural network can predict a likely overall base calling quality.

BRIEF DESCRIPTION OF THE DRAWINGS

The included drawings are for illustrative purposes and serve only to provide examples of possible structures and process operations for one or more implementations of this disclosure. These drawings in no way limit any changes in form and detail that may be made by one skilled in the art without departing from the spirit and scope of this disclosure. A more complete understanding of the subject matter may be derived by referring to the detailed description and claims when considered in conjunction with the following figures, wherein like reference numbers refer to similar elements throughout the figures.

FIG. 5 presents examples of subsystem performance data and overall base calling quality data stored in the sequencing quality database of FIG. 1.

DETAILED DESCRIPTION

Figure 1:
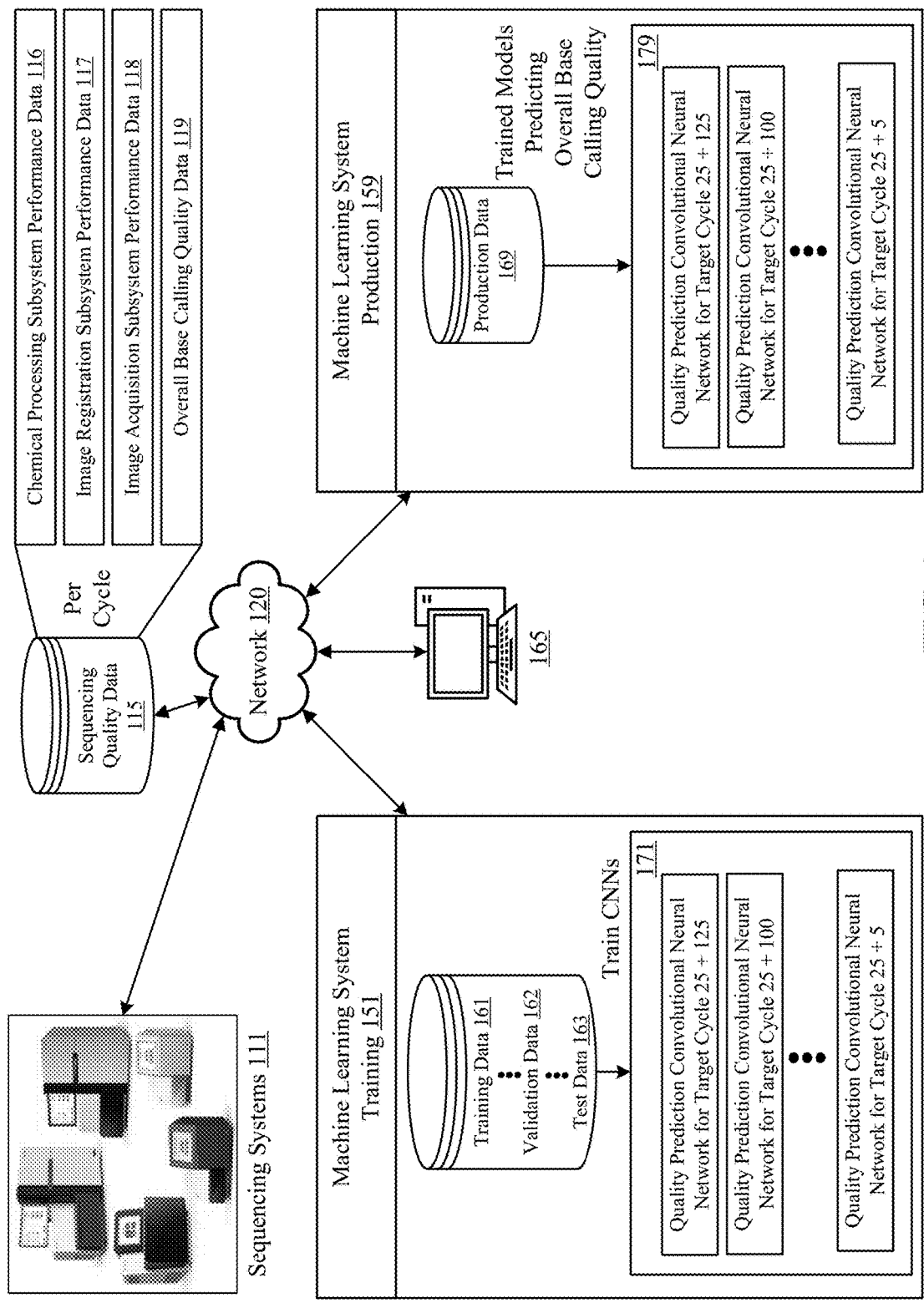
FIG. 1 shows an architectural level schematic of a system in which a machine learning system comprising quality prediction convolution neural network(s), predicts overall base calling quality of sequencing data generated by sequencing systems.

The following detailed description is made with reference to the figures. Sample implementations are described to illustrate the technology disclosed, not to limit its scope, which is defined by the claims. Those of ordinary skill in the art will recognize a variety of equivalent variations on the description that follows.

Introduction

The quality of base calls is a measure of success in sequencing nucleotides in a DNA or RNA molecule. Sequencing-by-synthesis (SBS) is one technique of sequencing that involves adding complementary nucleotides, one at a time, to a nucleotide sequence fragment from the DNA to be sequenced. An optical platform using SBS can sequence billions of clusters of nucleotide sequence fragments, sometimes called molecules, on a single slide or flow cell, arranged in multiple lanes with tiles in each lane. Molecule clusters present clones of a molecule. Cloning a molecule amplifies signals generated during SBS.

Sequencing nucleotides in molecules proceeds in hundreds of cycles. Before the cycles begin, clusters of the clones are readied for the SBS process. In a cycle, there are chemical, image capture and image processing actions. Chemical actions are designed to add one dye-tagged complementary nucleotide to each molecule in each cluster in each cycle. When a molecule falls behind or gets ahead of SBS for other molecules in its cluster, it is out of phase called phasing or pre-phasing. Image capture actions involves aligning a camera over a tile in a lane, illuminating the tile, and capturing one to four images. Image processing yields base calling, which means identifying the complementary nucleotide added to the molecules in a cluster during a cycle. The dye chemistry, illumination, camera design and number of images captured vary among sequencing platforms. Sequencing instruments can deliver subsystem performance measures for chemistry, camera positioning or registration, image capture or acquisition and overall base calling quality.

Sequencing a molecule of 350 nucleotides by SBS can involve 300 or more processing cycles in a run. Run are divided into two reads proceeding from the 3' and the 5' ends of the same sequence fragment. When the number of cycles is fewer than the length of the molecule, an unsequenced area will remain in the middle of the molecule after the reads from the 3' and the 5' ends.

Sequencing a human genome requires parallel sequencing of many DNA fragment molecules because the human genome contains approximately 3 billion base pairs. These base pairs are organized in 23 pairs of human chromosomes that are reproduced in each cell. The 300 cycles and subsequent processing to combine the partial sequences into an overall genome can take three days or more to complete. Some runs fail, due to quality problems. Reliably predicting the final quality of a sequencing run after a handful of cycles would benefit users of sequencing instruments, by allowing them to halt a bad run after half a day or less.

Operators of sequencing instruments cannot predict the final quality of a sequencing run early along. Fortunately, large sets of subsystem performance data are available that have been collected for performing trouble shooting. This subsystem data can be combined and used to predict the overall base calling quality at the end of a sequencing read or run and at intervals during a read. Using the subsystem performance metrics reported early in a run, a trained deep neural network can predict a likely overall base calling quality.

A similar, even earlier prediction can be made for a second read when a run includes two reads from opposite ends of a molecule. Since the second read follows the first read, data for late in the first read can be combined with data from early in the second read. This can dramatically reduce the number of cycles needed in the second read. For instance, where a subsystem performance data is used for twenty five cycles during a first read, it can be enough to combine just five cycles of data in the second read with twenty cycles of data from the first read. Separate predictions can be made for the quality of first and second reads.

Environment

We describe a system for early prediction of base calling quality during an extended optical base calling process. There are four types of nucleotides in a DNA molecule—Adenine (A), Cytosine (C), Guanine (G), and Thymine (T). Base calling refers to the process of determining a nucleotide base (A, C, G, T) per cluster of DNA molecules in one cycle of the sequencing run. The system is described with reference to FIG. 1 showing an architectural level schematic of a system in accordance with an implementation. Because FIG. 1 is an architectural diagram, certain details are intentionally omitted to improve the clarity of the description. The discussion of FIG. 1 is organized as follows. First, the elements of the figures are described, followed by their interconnection. Then, the use of the elements in the system is described in greater detail.

FIG. 1 includes the system 100. The system 100 includes sequencing systems 111, a sequencing quality database 115, a machine learning system 151 in training mode, a machine learning system 159 in production mode, and an operator 165 monitoring the subsystem performance and quality of base calls. The technology disclosed applies to a variety of sequencing systems 111, also referred to as sequencing instruments or sequencing platforms. Some examples of sequencing systems 111 include Illumina's HiSegX™, HiSeg3000™, HiSeg4000™, NovaSeq 6000™, and MiSeqDx™. These sequencing systems are configured to apply sequencing-by-synthesis (SBS) technique for base calling.

In SBS, lasers are used to illuminate dye-tagged complementary nucleotide attached to each molecule in each cluster in each cycle. A camera takes images of tiles which are then processed to identify a nucleotide (A, C, G, T) attached to the molecules in a cluster. Some sequencing systems use four-channels to identify four types of nucleotides (A, C, G, T) attached to molecules per cycle. In such systems, four images are produced, each image comprising signals having a single distinct color per image. The four colors correspond to the four possible nucleotides present at a particular location. In another type of sequencing systems two channels are used to identify four types of nucleotides (A, C, G, T). In such systems, two images are taken per cycle. A first nucleotide type is detected in a first channel, a second nucleotide type is detected in a second channel, a third nucleotide type is detected in both the first, and the second channel and a fourth nucleotide type that lacks a dye-tagged label, is not, or minimally, detected in either channel.

The sequencing quality database 115 stores subsystem performance and overall base calling quality data per cycle. In one implementation, the sequencing quality database 115 stores chemical processing subsystem performance data 116, image registration subsystem performance data 117, image acquisition subsystem performance data 118, and overall base calling quality data 119. The sequencing quality database 115 stores these data per cycle of a specific sequencing system. The sequencing systems 111 sequence the molecules in a sequencing run. As described above, sequencing a molecule of 350 nucleotides using SBS involves 300 or more processing cycles in the sequencing run. A sequencing run is sometime divided into two reads proceeding for the 3' and the 5' ends of the same sequenced molecule (also referred to as a fragment or insert). This is also referred to as a paired-end read. In one type of sequencer, each of the two reads from opposite ends of a molecule each involves 150 base calling cycles. The number of cycles per read can be more of less than 150, varying by sequencer model. The technology disclosed divides the total cycles in each read into pre-prediction and post-prediction cycles. In one implementation of the system 100, the first 25 cycles of read 1 are the pre-prediction cycles and the following 125 cycles are the post-prediction cycles. Read 2 has even fewer pre-prediction cycles. In one implementation, the first 5 cycles of read 2 are pre-prediction cycles and the following 145 cycles are post-prediction cycles. It is understood that fewer or more cycles in each read can be used as pre-prediction and post-prediction cycles respectively.

The machine learning system 151 comprises a database containing training data 161, validation data 162, and test data 163. The three data sets contain data from the sequencing quality database 115 for the subsystems' performance and overall base calling quality from prior sequencing runs of the sequencing systems 111. The data is organized per cycle indicating the subsystem performance in pre-prediction base calling process cycles and overall base calling quality for all cycles of a sequencing run. These data sets are used to train and test the performance of quality prediction convolutional neural networks 171. Each quality prediction convolutional neural network comprises one or more convolutional neural networks (CNNs) and fully connected (FC) networks. In the training mode of the machine learning system 151, forward passes and backpropagations are used as opposed to production mode of the machine learning system 159 which performs forward passes only. In a forward pass, the machine learning system predicts the likely overall base calling quality expected at a target post-prediction base calling process cycle. In the backpropagation, the machine learning system calculates a gradient for one or more cost functions and propagates the gradient(s) to the CNN and the FC neural network during training.

In one implementation of the system 100, the machine learning system 151 comprises one quality prediction convolutional neural network 171. This quality prediction convolutional neural network 171 predicts the likely overall base calling quality expected at the end of post-prediction base calling process cycles for a read. In one implementation of the system 100, the number of post-prediction cycles of a read are at least two times as much as the number of pre-prediction base calling process cycles. In another implementation of the system 100, the quality prediction convolutional neural network 171 predicts the likely overall base calling quality for at least five intermediate cycle counts during the post-prediction base calling process cycles. The quality prediction convolutional neural network 171 outputs the intermediate likely overall base calling quality determinations for each of the five intermediate cycles. In another implementation of the system 100, the quality prediction convolutional neural network 171 predicts a likely overall base calling quality expected at each post-prediction cycle of a read.

In another implementation of the system 100, the machine learning system 151 comprises multiple quality prediction convolutional neural networks 171. Each quality prediction convolutional neural network is separately trained using training data 161 comprising the subsystems' performance time series and an overall base call calling quality time series for the pre-prediction base calling process cycles and a post-prediction overall base calling quality time series for a target cycle. In such an implementation of the system 100, a particular trained convolutional neural network determines, from the pre-prediction base calling process cycles, a likely overall base calling quality expected at a target cycle. A target cycle can be the last cycle of a read or any of the intermediate cycles in the post-prediction cycles. In FIG. 1, the example machine learning system 151 comprises a quality prediction convolutional neural network for target cycles at an increment of 5 or 10 cycles up to the last cycle, for instance the $100^{th}$ or $150^{th}$ base calling cycle in a read The trained quality prediction convolutional neural networks 179 are deployed in production mode and are shown as part of machine learning system 159 in FIG. 1. The machine learning system 159 further comprises a production database 169. The production database 169 contains subsystems' performance data 116, 117, 118 and overall base calling quality data 119 per pre-prediction cycle of a sequencing system. The trained quality prediction convolutional neural networks 179 determine, from the pre-prediction base calling process cycles, a likely overall base calling quality expected after at least two times as many post-prediction base calling process cycles as the pre-prediction cycles. As discussed above, in one implementation of the system 100, a single trained quality prediction convolutional neural network 179 can be used to predict the expected overall base calling quality for multiple target cycles in the post-production cycles of a read of the sequencing data. In another implementation of the system 100, a separate trained quality prediction convolutional neural network for each target cycle is used as shown in FIG. 1. The machine learning system in training 151 and production 159 can run on a variety of hardware processors such as graphic processor units (GPUs). Neural network-based models involve computationally intensive methods, such as convolutions and matrix-based operations. GPUs are well suited for these types of computations. Recently, specialized hardware is being developed to efficiently train neural network models.

Sequencing Quality Data

Figure 2:
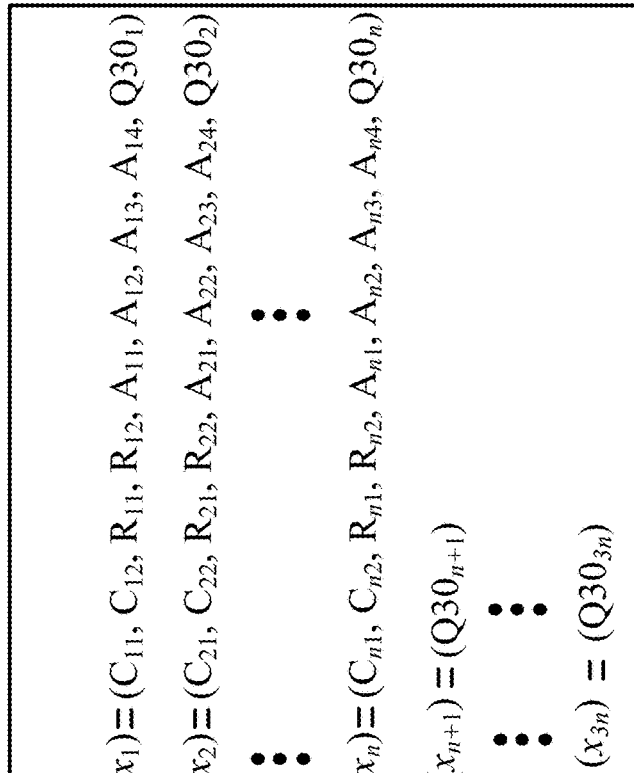
FIG. 2 illustrates subsystem performance and overall base calling quality data stored per cycle in sequencing quality database of FIG. 1.

FIG. 2 shows sequencing quality metrics 213 stored in the sequencing quality database 115 per cycle of the sequencing run of a specific sequencing system 200. FIG. 2 lists some example subsystem performance metrics at a higher level of abstraction. These metrics include chemical processing subsystem performance data 116, image registration subsystem performance data 117, and image acquisition subsystem performance data 118. The overall base calling quality data 119 per cycle is also given as input to the machine learning system. In FIG. 2, the subsystem performance data 116, 117, and 118 for "n" sequencing cycles of a read of a sequencing run are shown for illustration purposes. The total number of cycles in a read are shown are "3n". The first "n" sequencing cycles are the pre-prediction cycles and the following "2n" cycles are the post-prediction cycles in a read of a sequencing run.

The sequencing quality data per cycle 219 shows the subsystem performance metrics at a lower level of abstraction. The chemical processing subsystem performance data 116 includes two metrics shown as a phasing measure $C_{n1}$ and prephasing measure $C_{n2}$ for the first "n" cycles of a sequencing run. During each cycle of sequencing-by-synthesis (SBS) technique, a chemical process attaches a complementary nucleotide to a target nucleotide strand (or a molecule) at millions of locations on a substrate. The term "phasing" describes a situation in which a molecule in a cluster of molecules falls at least one base behind other molecules in the same cluster during the sequencing process. This results due to an incomplete chemical reaction. The molecules sequence out of phase with the rest of the cluster. More specifically, these molecules lag a cycle behind other molecules in the cluster. The effect is cumulative, once a molecule falls behind, it cannot catch up with the rest of the molecules in the cluster. More molecules may fall behind in the next cycle.

The term "prephasing" refers to a situation in which a molecule jumps at least one base ahead of other molecules in the same cluster of molecules. One reason for pre-phasing is the incorporation of an unterminated nucleotide, and subsequent incorporation of a second nucleotide in the same sequencing cycle. The sequencing quality data 219 includes phasing measure and prephasing measure for pre-prediction cycles of a read. In an implementation of the system 100, a sequencing run has two reads, the value of "n" is "25" for read 1 and "5" for read 2 of a sequencing run. It is understood, that different number of cycles can be used as pre-prediction cycles in read 1 and read 2.

In implementations, sequencing systems 111 provide two types of cluster arrangements on tiles of a flow cell, referred to as random and patterned. The sequencing systems 111 use a camera to capture the image of clusters per tile on the flow cells during a sequencing cycle. The process of aligning a virtual image (also referred to as a template) onto a given sequencing image is referred to as registration. For image registration with random arrangement of cluster positions on flow cells, a template is generated in the first few cycles (for example 5 cycles) of a sequencing run which identifies the locations (x and y positions) of clusters on the flow cell. The image registration subsystem performance data includes "x" offset adjustment $R_{n1}$ and "y" offset adjustment $R_{n2}$ of cluster locations in the image for the first "n" cycles, also referred to as pre-prediction cycles of a read of a sequencing run.

Alternatively, a second cluster formation technique used by the sequencing systems 111 is based on patterned flow cells. The patterned flow cells have arrays of nanowells that allow higher cluster densities and unambiguous cluster identification. For flow cells with patterned location of clusters, the template generation process is replaced by a step where a hexagonal packed lattice of clusters is placed on x, y positions on an area corresponding to the size of the tile. The virtual image (or template) is replaced by a virtual image of a ring fiducial which is correlated to a portion of the sequencing image containing the actual ring fiducial. The image registration subsystem performance data in such sequencing systems is the same as presented above for sequencing systems with random arrangement of cluster positions.

During each cycle of the SBS technique, four types of complimentary nucleotides (A, C, G, T) are simultaneously delivered to the clusters of molecules on the tiles arranged in lanes on flow cells. Each nucleotide has a spectrally distinct label attached to it. Lasers are used to illuminate dye-tagged complementary nucleotide attached to each molecule in each cluster in each cycle. A camera takes images of tiles which are then processed to identify a nucleotide (A, C, G, T) attached to the molecules in a cluster. Some sequencing systems use four-channels to identify four types of nucleotides (A, C, G, T) attached to molecules per cycle. In such systems, four images are produced, each image comprising signals having a single distinct color per image. The four colors correspond to the four possible nucleotides present at a particular location. Four images are then obtained, each using a detection channel that is selective for one of the four different labels. Bases are then called for each cluster using the identified label. In such an implementation, four values (one per channel) of "x" offset adjustment $R_{n1}$ and "y" offset adjustment $R_{n2}$ for a cycle "n" are given as input to the machine learning system.

In another type of sequencing systems two channels are used to identify four types of complimentary nucleotides (A, C, G, T) attached to molecules. In such systems, two images are taken per cycle. A first nucleotide type is detected in a first channel, a second nucleotide type is detected in a second channel, a third nucleotide type is detected in both the first and the second channel and a fourth nucleotide type that lacks a dye-tagged label, is not, or minimally, detected in either channel. As mentioned above, the sequencing quality data 219 includes image registration subsystem performance data for the first "n" cycles, also referred to as the pre-prediction cycles of a read of a sequencing run.

The image acquisition subsystem performance data includes focus score $A_{n1}$, minimum contrast measure $A_{n2}$, maximum contrast measure $A_{n3}$, and intensity measure $A_{n4}$ for the first "n" cycles of a sequencing run. The focus score is defined as the average full width of clusters of molecules at half maximum (FWHM) representing their approximate size in pixels. The minimum contrast and maximum contrast values are the $10^{th}$ and $99.5^{th}$ percentiles per channel of selected columns of the raw image, respectively. A selected column can be a specific tile or a lane of the flow cell. The process of determining an intensity value for each cluster in the template for a given sequencing image is referred to as intensity extraction. To extract intensity, a background is computed for a cluster using a portion of the image containing the cluster. The signal for the background is subtracted from the signal for the cluster to determine the intensity. An extracted intensity from the $90^{th}$ percentile of the data is stored in the sequencing quality data 219. The image acquisition subsystem performance data for the first "n" pre-prediction cycles of a read for a sequencing run are stored in the sequencing quality database 219. In one implementation, each of the image acquisition subsystem performance data values comprises four values corresponding to the four channels as discussed above.

The overall base calling quality data 119 is given as input Q30 for all "3n" cycles in a read of a sequencing run. Quality scoring is a widely-used technique in DNA sequencing and is used to determine the confidence in the correctness of a base call, thereby assigning a Phred quality score. For example, a pre-trained instrument specific model is used to derive the quality of the base call at each cycle of a sequencing system (also called as sequencing instrument) by Illumina Inc. Percentage of bases above Q30 (also written as % Q>30) implies the percentage of base calls that have a quality score of 30 or higher. A quality score of 30 in turn represents a three nines accuracy of base calls, or indicating a base call accuracy of 99.9%. Likewise, a quality score of 20 means a 99% accuracy of base calls. A quality score of 40 indicates a 99.99% accuracy of base calls. During the course of a sequencing run, % Q>30 metric can be viewed at various levels such as for each tile per cycle, or as an average across all tiles for a lane per cycle, or as an average for all tiles per cycle and also as a "global" average of the entire sequencing run.

A quality of a run can be judged by % Q>30 values, with higher % Q>30 values indicating higher number of bases that can be reliably used for downstream data analysis. Each Illumina Inc. sequencing system has an expected % Q>30 specification. For example, for HiSegX™ system, on average, greater than or equal to 75% of bases are expected above Q30 for sequencing paired-end reads with read length of 150 nucleotides (also referred to as bases). In one implementation of the system 100, during training the overall base calling quality for each post-prediction sequencing cycle (Q30n+1 to Q303n) is the average of ten cycles. For example, overall base calling quality value fora post-prediction cycle 50 is the average of overall base calling quality values for cycles 45 to 54.

The subsystem performance data 116, 117, and 118 for the pre-prediction cycles ("n") and the overall base call calling data 119 for all cycles ("3n") of a read are stored in the sequencing quality database 219. In one implementation of the system 100, additional sequencing quality metrics are used as input the machine learning system. Examples of such metrics include data reported by temperature sensors in the flow cells and laser power sensors. The data reported by sensors in the sequencing systems 111 is used to monitor the system performance during a sequencing run. Sometimes, data reported by the sensors can also include data before and after a sequencing run. Further examples of metrics that can be used as input to the machine learning system include, error metrics per cycle containing cycle error rate as well as counts for perfect reads and read with one to four errors. It is understood that additional metrics can be included as input to the machine learning system for predicting the overall base calling quality of a sequencing run.

Quality Prediction Convolutional Neural Networks

Figure 3:
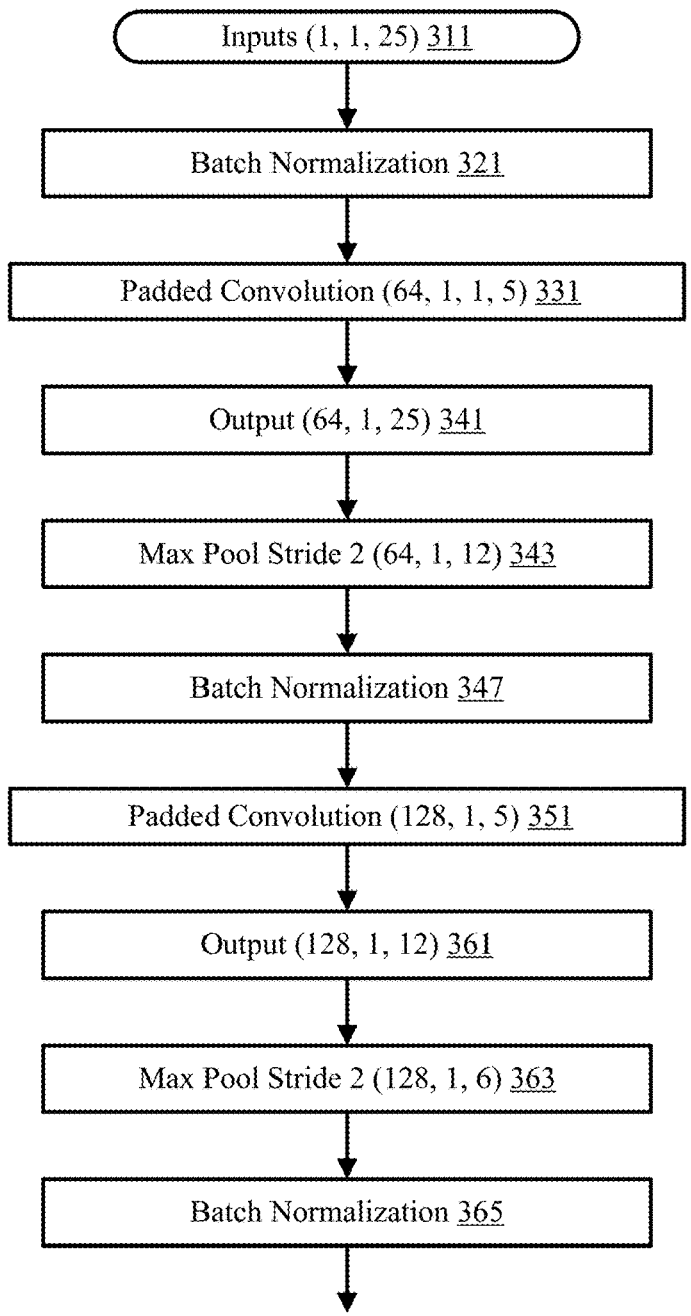
FIG. 3 illustrates processing of inputs with one channel by different layers of a quality prediction convolutional neural network of FIG. 1.

FIG. 3 illustrates layers of the quality prediction convolutional neural network (CNN) 300 of FIG. 1. FIG. 3 is an implementation with two convolution layers. This network can have one to five convolution layers. In other implementations, this network can have more than five convolution layers. One way to analyze the output of the convolution is through a fully connected (FC) network. Therefore, the outputs of the convolution layers is given to FC network(s) in the last layers of the quality prediction CNN. The fully connected layers can be implemented as a multi-layer perception with two to five layers. One output from the FC network(s) can be used for predicting the likely overall base calling quality expected at a specific target cycle in post-prediction cycles of a read. In such an implementation of the system, a separate machine learning system is trained to predict the likely overall base calling quality expected at each target cycle. In an alternate implementation of the machine learning system, multiple outputs from the FC network(s) can be used to predict the overall base calling quality expected at multiple post-prediction target cycles.

In FIG. 3, the dimensionality of inputs at each layer of the quality prediction CNN is indicated in parenthesis. As discussed above, some inputs to the quality prediction CNN have one channel while others can have four channels. The example quality prediction CNN shown in FIG. 3 is used for inputs with one channel. The dimensionality of the input time series shows that there are twenty five inputs with each input value comprising of one value with one dimension (311). This input can be imagined as a one dimensional vector containing twenty five real numbers. The twenty five values correspond to a specific subsystem performance. For example, the chemical processing subsystem performance time series or the overall base calling quality time series. As discussed above both of these inputs have one channel per cycle. Each input passes through independent convolutions. The input is then passed through a batch normalization layer at block 321.

Distribution of each layer in a convolution neural network (CNN) changes during training and it varies from one layer to another. This reduces the convergence speed of the optimization algorithm. Batch normalization (Ioffe and Szegedy 2015) is a technique to overcome this problem. Denoting the input of a batch normalization layer with x and its output using z, batch normalization applies the following transformation on x:

$$z = \frac{x - \mu}{\sqrt{\sigma^2 + \varepsilon}} \gamma + \beta$$

Batch normalization applies mean-variance normalization on the input x using $\mu$ and $\sigma$ and linearly scales and shifts it using $\gamma$ and $\beta$. The normalization parameters $\mu$ and $\sigma$ are computed for the current layer over the training set using a method called exponential moving average. In other words, they are not trainable parameters. In contrast, $\gamma$ and $\beta$ are trainable parameters. The values for $\mu$ and $\sigma$ calculated above during training are used in forward pass during production.

The output from the batch normalization layer 321 is given as input to convolution layer 331. Batch normalization does not change the dimensionality of the input. In the example of convolution layer shown in FIG. 3, sixty four filters of width 5 and height 1 are convolved over the input which is padded with two zeros on each side. Zero-padding is used to handle the borders during convolution. Zero-padding a H×W input with pad=2 can be thought as creating a zero matrix of size (H+2pad)×(W+2pad) and copying the input into this matrix such that it is placed exactly in the middle of the zero matrix. If the size of convolution filters is (2pad+1)×(2pad+1), the result of convolution with zero-padded input with be H×W which is exactly equal to the size of input. Padding is usually done for keeping the size of input and output of convolution operations constant.

The output of the first convolution layer 331 comprises 25 values each having sixty four channels and one width. The output of the convolution is also referred to as feature maps. This output is given as input to a max pool layer 343. The goal of a pooling layer is to reduce the dimensionality of feature maps. For this reason, it is also called "downsampling". The factor to which the downsampling will be done is called "stride" or "downsampling factor". The pooling stride is denoted by "s". In one type of pooling, called "max-pool", the maximum value is selected for each stride. For example, consider max-pooling with s=2 is applied to a 12-dimensional vector x=[1, 10, 8, 2, 3, 6, 7, 0, 5, 4, 9, 2]. Max-pooling vector x with stride s=2 means we select the maximum value out of every two values starting from the index 0, resulting in the vector [10, 8, 6, 7, 5, 9]. Therefore, max-pooling vector x with stride s=2 results in a 6-dimensional vector. Max pool layer 343 reduces dimensionality of output 341 of first convolution from twenty five values to twelve values using a stride of s=2. The value at the twenty fifth position in output 341 is discarded.

The output of max pool layer 343 is passed through a batch normalization layer 347 before given as input to a next convolution layer 351. In the convolution layer, sixty four kernels of size five by 1 (5×1) convolve over the sixty four dimensions respectively, to produce an output feature map of size sixty four by twelve (64×12). A sum operation is performed across the sixty four dimensions to produce a feature map of size one by twelve (1×12). This convolution layer has 128 kernels, therefore, above operations are performed 128 times, producing an output feature map with dimensions one hundred twenty eight by twelve (128×12). As discussed above, the second convolution layer also operates on input that has two-zero padding on each side. The output of second convolution layer is shown in block 361. A max pool layer 363 with stride s=2, reduces the output of convolution from to six values having one hundred and twenty eight channels per value which is passed through a third batch normalization layer at block 365. The output from batch normalization layer 365 is given to a summing layer followed by two fully connected (FC) networks. Details are of these layers presented in FIG. 4.

Dropout is a simple but effective technique to prevent a neural network from overfitting. It works by randomly dropping a fraction of neurons from the network in each iteration of the training. This means that output and gradients of selected neurons are set to zero so they do not have any impact on forward and backward passes. In the example, quality prediction convolutional neural network shown in FIG. 3, dropout is performed before the second and third batch normalization layers 347 and 365 respectively, using a probability of 0.3.

Figure 4:
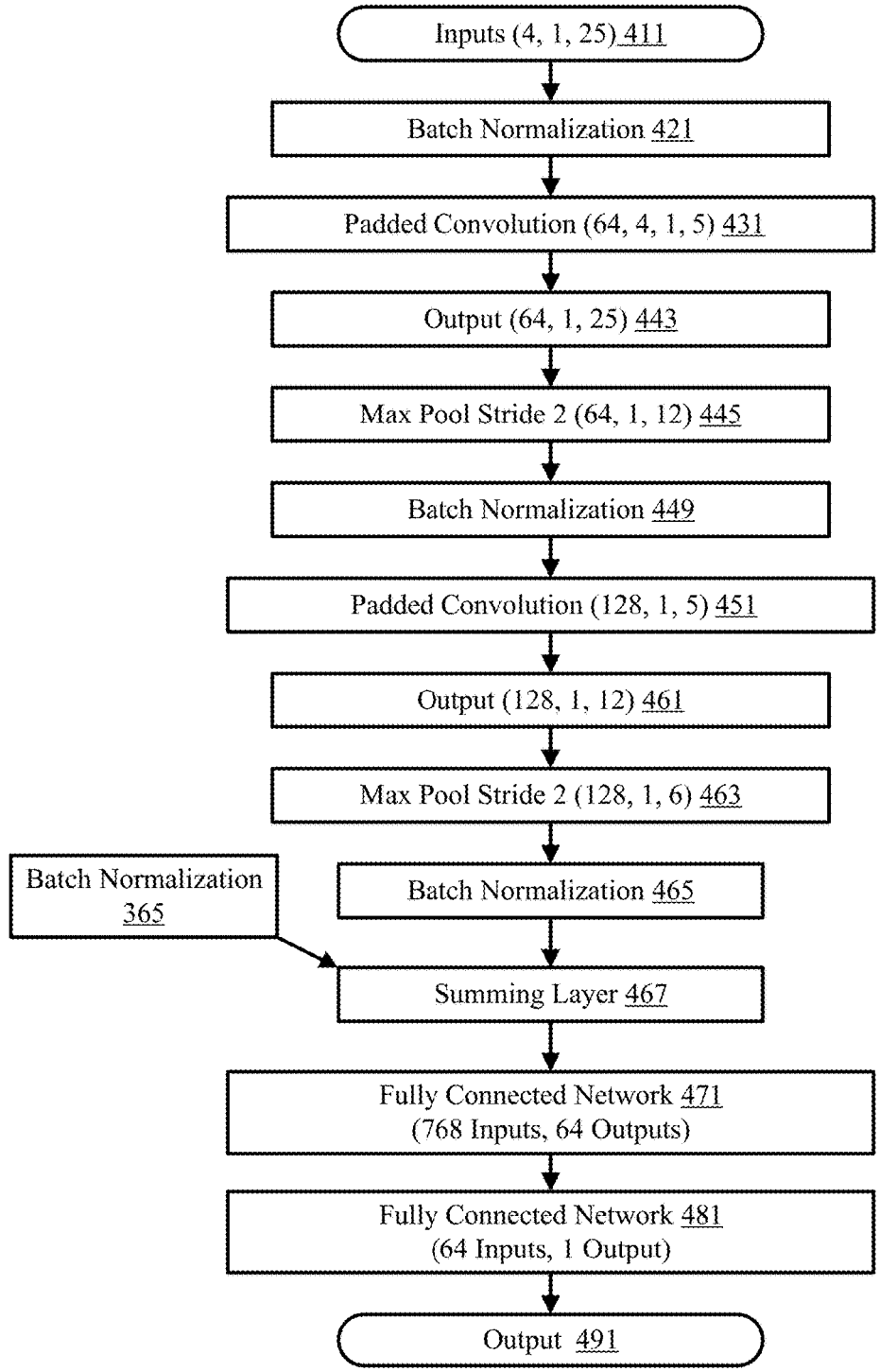
FIG. 4 illustrates processing of inputs with four channels by different layers of a quality prediction convolutional neural network of FIG. 1.

FIG. 4 illustrates architecture of an example quality prediction convolutional neural network (CNN) 400 similar to the network presented in FIG. 3 but it is designed for inputs with four channels. As discussed above, the image registration subsystem performance time series and image acquisition subsystem performance time series consist of data with four channels. The channels can correspond to the four types of nucleotides (A, C, G, T). In one implementation of the quality prediction CNN, the four channels per input are combined before the input is processed by the quality prediction CNN. In another implementation of the network, the quality prediction CNN takes the inputs with four channel and produces outputs with four channels corresponding to the input. The four channels per output value from the quality prediction CNN are added resulting in a value with one channel. In either implementation, a sum operation that adds the values in four channels per input value can be used. In the example network shown in FIG. 4, the convolution filters are convolved on inputs with four channels.

The input 411 comprises twenty five values corresponding to the twenty five pre-prediction cycles in a read of a sequencing run. Each of the twenty five input values is of size one and has four channels. At block 421 batch normalization is performed on the input. A padded convolution with the two-zero padding is performed at block 431. Four kernels of size five by one (5×1) convolve over the four channels producing a feature map of size four by twenty five (4×25). A sum operation is performed across the four dimension to produce a feature map of size one by twenty five (1×25). The above operations are performed sixty four (64) times as there are 64 kernels producing an output of dimensions sixty four by twenty five (64×25) as shown in block 443. A max pool of stride s=2 is performed at block 445 resulting in sixty four feature maps of size twelve. The output of max pool layer is passed through a second batch normalization at block 449.

A second convolution is performed at block 451 with one hundred and twenty eight filters of size five. The second convolution convolves the filters over input with two-zero padding on each side. The output of the second convolution comprises one hundred and twenty eight feature maps of size twelve as shown in block 461. At block 463, max pool with a stride s=2 reduces the dimensionality to one hundred and twenty eight feature maps of size six. A third batch normalization is performed at block 465. The outputs from convolutions of all inputs (465 and 365) are summed at the summing layer 467. The inputs to the summing layer 467 are nine features maps corresponding to nine input features. Dimensions of each feature map are six times one hundred and twenty eight (6×128). The summing layer 467 sums up the nine features to reduce the dimensionality to 768 inputs (6×128). The output of summing layer 467 is then passed to a first fully connected (FC) network 471 after flattening. FC 471 produces sixty four outputs which are given as input to a second FC network 481 producing one output 491. The output 491 predicts the likely overall base calling quality for a target cycle for operator 165.

Examples of Subsystem Performance Data

FIG. 5 shows example data 500 for chemical processing subsystem performance 116, image registration subsystem performance 117, image acquisition subsystem performance 118 and the overall base calling quality 119. The data is arranged according to the performance measures per subsystem. For example, the chemical processing subsystem performance data 116 includes phasing and prephasing measures. Similarly the image registration subsystem performance data 117 includes translation x and translation y measures. The image acquisition subsystem performance data 118 includes intensity, maximum contrast, minimum contrast and focus score measures. The overall base calling quality data 119 indicates the percentage of base calls above Q30 quality measure. In one implementation of the system, the above mentioned data for 23,000 sequencing runs from HiSeqX, HiSeq3000 and HiSeq4000 sequencing machines from Illumina Inc. is used to train the quality prediction convolution neural networks 171.

Analysis of Base Calling Quality Prediction Results

Figure 6:
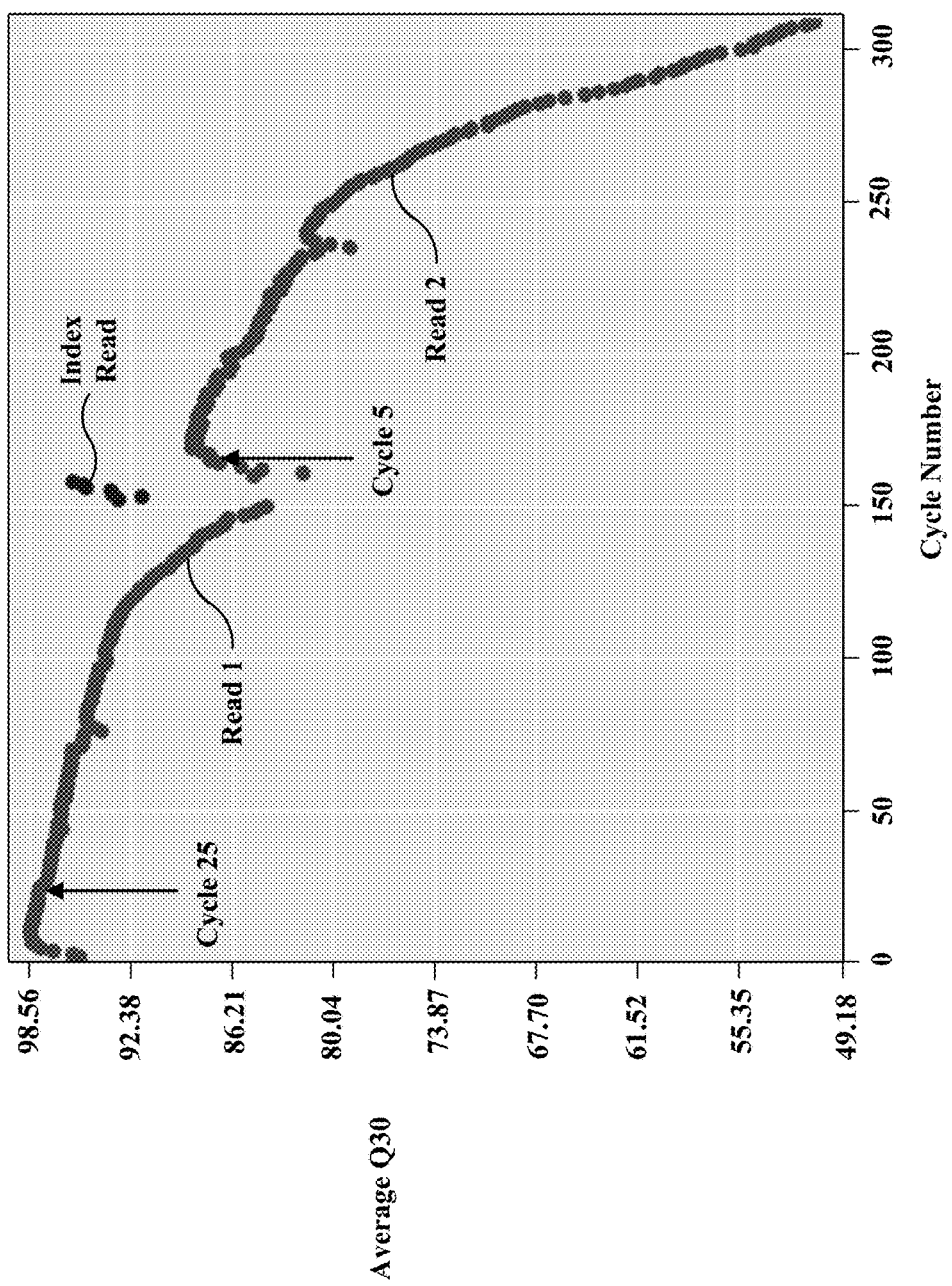
FIG. 6 shows a graphical representation of overall base calling quality data for two reads of an example sequencing run.

FIG. 6 comprises a graph 600 illustrating the average overall base calling quality results (Q30) for an example sequencing run in a sequencing system. The sequencing run comprises pair-ended reads: read 1 and read 2. Each read comprises 150 base calls corresponding to 150 sequencing cycles in which one complementary nucleotide is attached to molecules in clusters arranged on tiles on flow cells. The two reads are separated by an index read. In some sequencing runs, molecules from multiple source DNA samples are sequenced together. The index read is used to identify the sequencing data belonging to unique source DNA samples.

In one implementation, first 25 cycles of read 1 and first 5 cycles of read 2 are used as pre-prediction base calling process cycles. The subsystem performance data 116, 117, and 118 and overall base calling quality data 119 from pre-prediction cycles is given as input to the quality prediction convolutional neural networks (CNNs). In another implementation, the overall base calling quality score from the last 20 cycles of read 1 is also given as an input to the quality prediction CNNs for read 2. Graph 600 shows that the average Q30 score for the example sequencing run decreases as the molecules are sequenced. Because the chemical processes performed in sequencing cycles area stochastic process, the errors in chemical processing steps in each cycle accumulate. As more sequencing cycles are performed, the errors in previous cycles are summed up to create the fall-off indicated by the curves for read 1 and read 2 in the graph 600.

Figure 7:
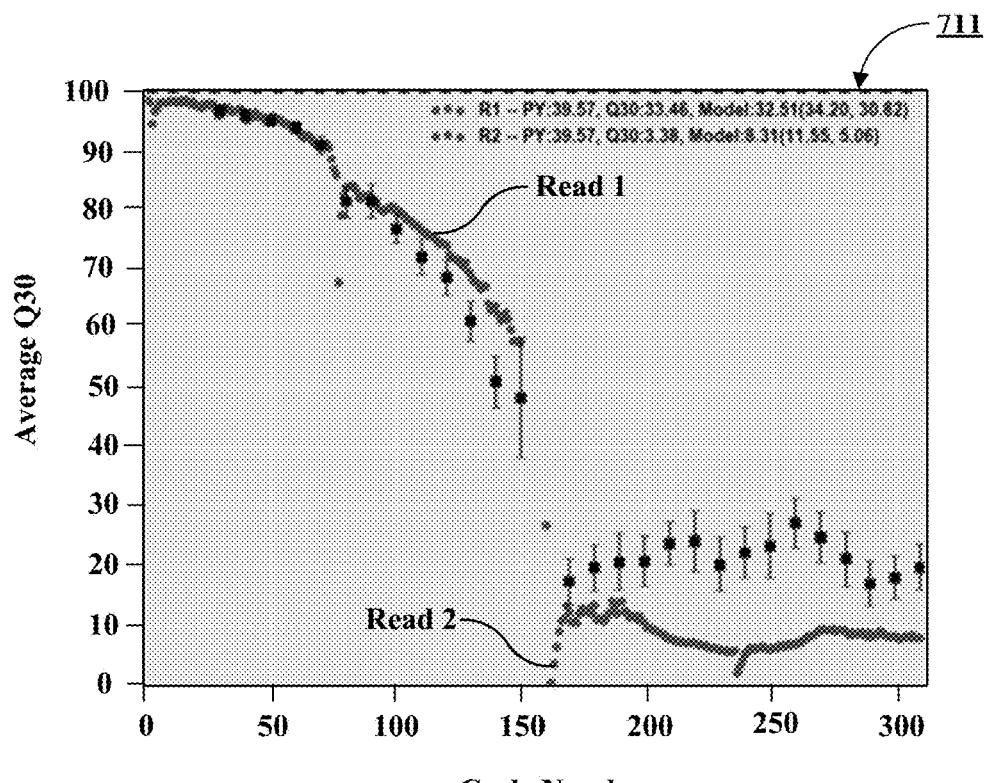
FIG. 7 illustrates overall base calling quality data for two reads of two example sequencing runs indicating predicted overall base calling quality at different target cycles.
Figure 7:
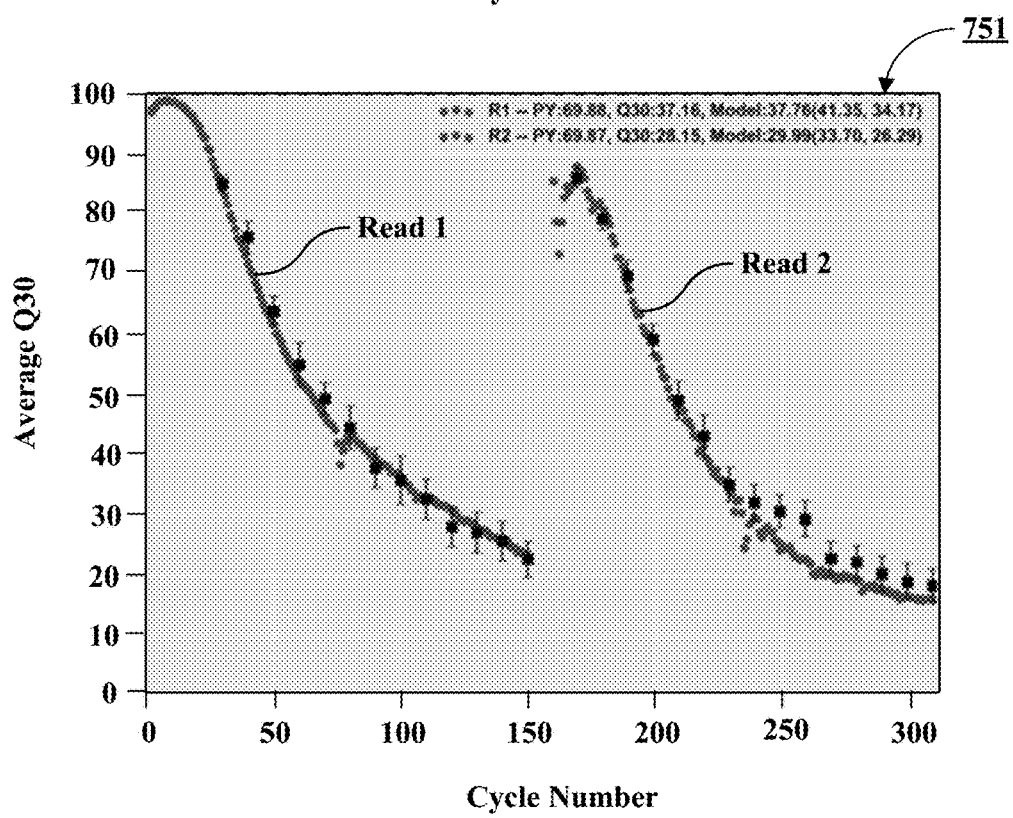

FIG. 7 shows the overall base calling quality prediction results 700 along with the confidence intervals for two example paired-ended sequencing runs shown in graphs 711 and 751. The actual average Q30 values for both sequencing runs are shown as read 1 and read 2 plots. Trained quality prediction convolutional neural networks (CNNs) 179 output the likely overall base calling quality of cycle 150 which is the last cycle of read 1. The quality prediction CNNs also predict the base calling quality of intermediate cycles starting at cycle 30 and continuing up to cycle 150 at intervals of 10 sequencing cycles, such as cycles 30, 40, 50, 60 to end of the read. The predicted values are indicated in boxes along with confidence intervals of each prediction.

In implementations, an ensemble of three trained quality prediction convolutional neural networks (CNNs) 179 is used during production (also referred to as "inference") to predict the likely overall base calling quality for a target cycle. Each one of the three models is run 100 times to generate as many prediction values, according to one implementation. The mean of the total 300 prediction values generated by the three quality prediction CNNs is then used as the final prediction result. The standard deviation of the predicted value is used as a confidence interval. The reads with overall base calling quality values close to training data can have a low uncertainty or a tight confidence interval. The prediction results far away from training examples can have higher uncertainty.

During training, the overall base calling quality data 119 per cycle can be best approximated by an average of ten sequencing cycles, according to one implementation. For example, the overall base calling quality data for cycle 50 is an average of the overall base calling quality data for cycles 45 to 54. In such an implementation, during production, the quality prediction CNNs, predict the average (across ten cycles) overall base calling quality for each target cycle. This is because it may be difficult to ascertain the performance of quality prediction CNNs for one specific target cycle due to fluctuations in one single cycle. For example, one specific cycle, say cycle 50 is bad but the cycles before and after are not that bad. Therefore, an average of ten cycles can be used to predict the overall base calling quality of a specific target cycle.

Graph 711 shows an implementation in which the quality prediction CNNs 179 are more confident in predicting average Q30 scores for earlier target cycles of read 1 as compared to later target cycles. The read 2 of this sequencing run has low average Q30 scores. Although the likely overall base calling quality scores predicted by CNNs 179 are higher than the actual read 2 results, the prediction results after the first five cycles of read 2 inform the operator 165 that likely overall base calling quality of read 2 is low.

Graph 751 shows an implementation in which the quality prediction CNNs 179 predicted the quality scores for target cycles with a high confidence and accuracy.

Using graphs 711 and 751, the operator 165 can decide to continue or terminate a sequencing run after reviewing the results of the quality prediction CNNs 179 early in the lifecycle of read 1 and read 2. In one implementation, the predicted scores along with confidence values are presented to the operator 165 at the end of cycle 25 for read 1 and at the end of cycle 5 for read 2.

Figure 8:
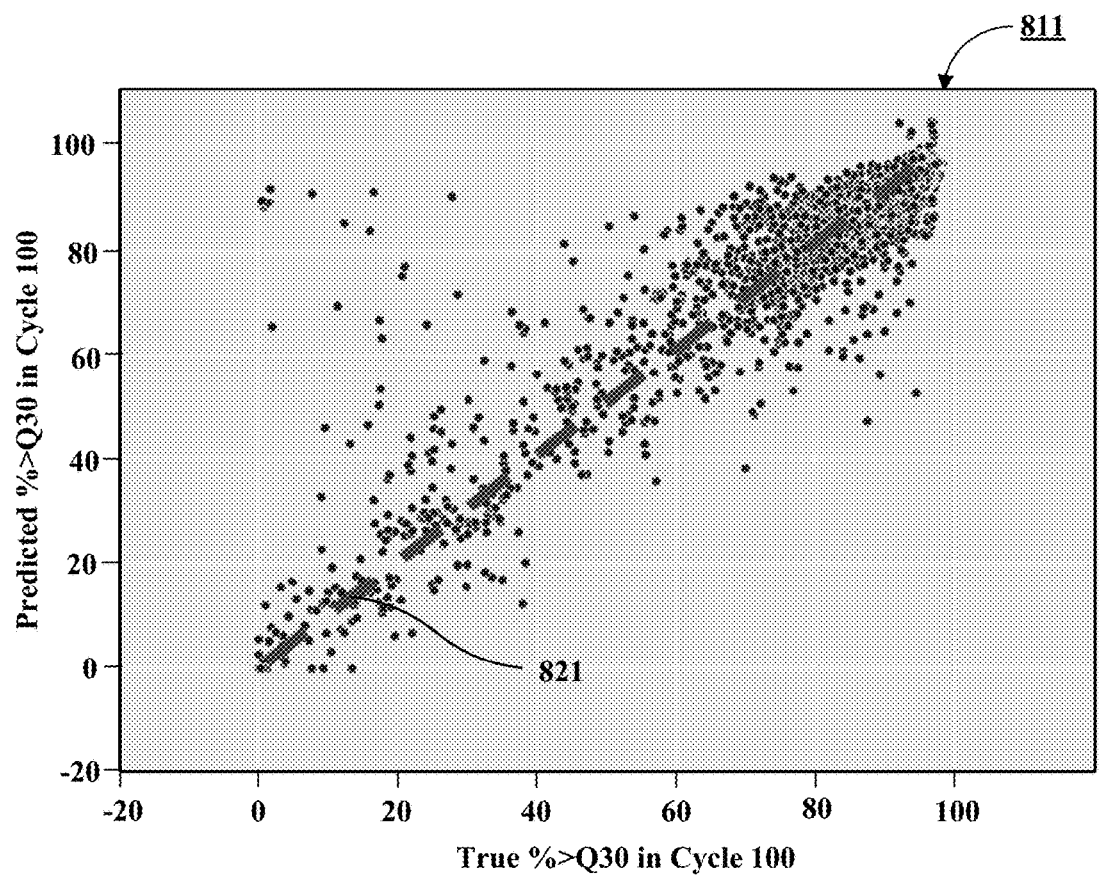
FIG. 8 presents graph of example data for predicted and true overall base calling quality data for a target cycle and comparison of validation and test data for intermediate target cycles.
Figure 8:
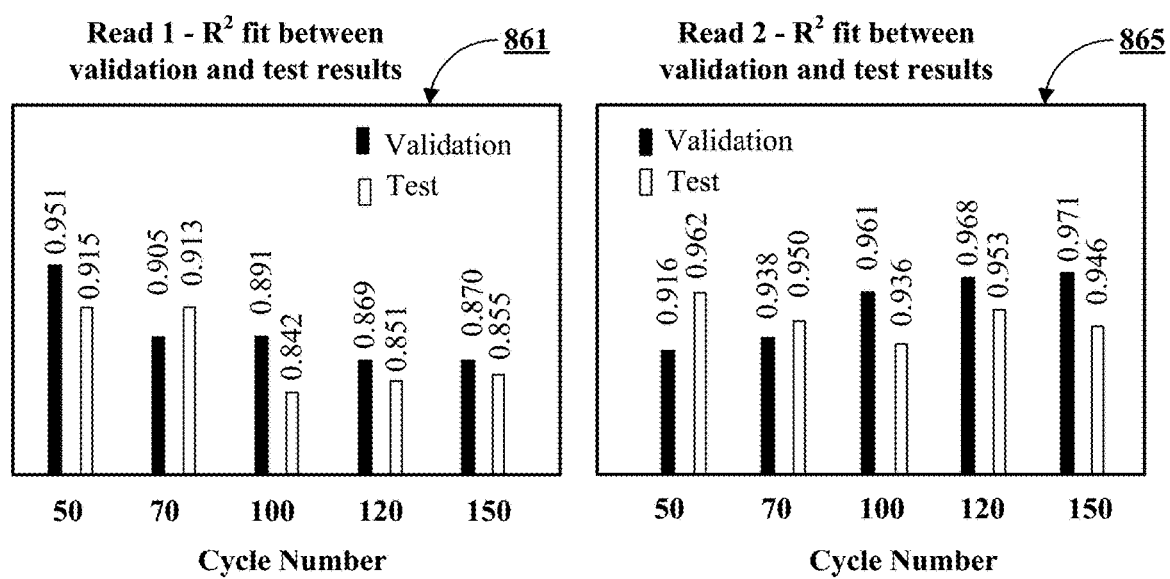

FIG. 8 presents a comparison 800 of true and predicted values of percentage of base calls above Q30 score (%>Q30) for cycle 100 in a graph 811. It is evident that a majority of data points are along a dashed line 821 which means predicted value is close to true value. There are a few data points at the top left corner of the graph 811 indicating a high predicted value as compared to the true value of percentage of base calls above Q30 score. As mentioned above, base calling is a stochastic process and each cycle involves several chemical processing steps. The predicted results of the quality prediction CNNs 179 are not close to true values in the few cycles on the top left corner of the graph. However, since the quality prediction CNNs predict Q30 scores for multiple target cycles, the operator 165 can use predicted values for all target cycles to make a decision about the sequencing run.

The graphs 861 and 865 show the performance of the quality prediction convolutional neural networks for read 1 and read 2 of an example sequencing run, respectively. The subsystems' performance metrics and overall base calling quality for the first 25 cycles is used to predict the likely overall base calling quality at target cycles 50, 70, 100, 120, and 150 for read 1. Likewise, the inputs for the first five cycles of read 2 are used to predict the likely overall base calling quality at the same target cycles for read 2.

Coefficient of determination, denoted as $R^2$ is the proportion of variance in the dependent variable that is predicted from the independent variables. It is a statistical measure of how well the prediction data approximates the real data points. An $R^2$ of "1" indicates that the regression data perfectly fits the true data. The graphs 861 and 865 show how close the model predictions for likely overall base calling quality are to the true values in validation and testing.

Training and Inference of Quality Prediction Convolutional Neural Networks

Figure 9:
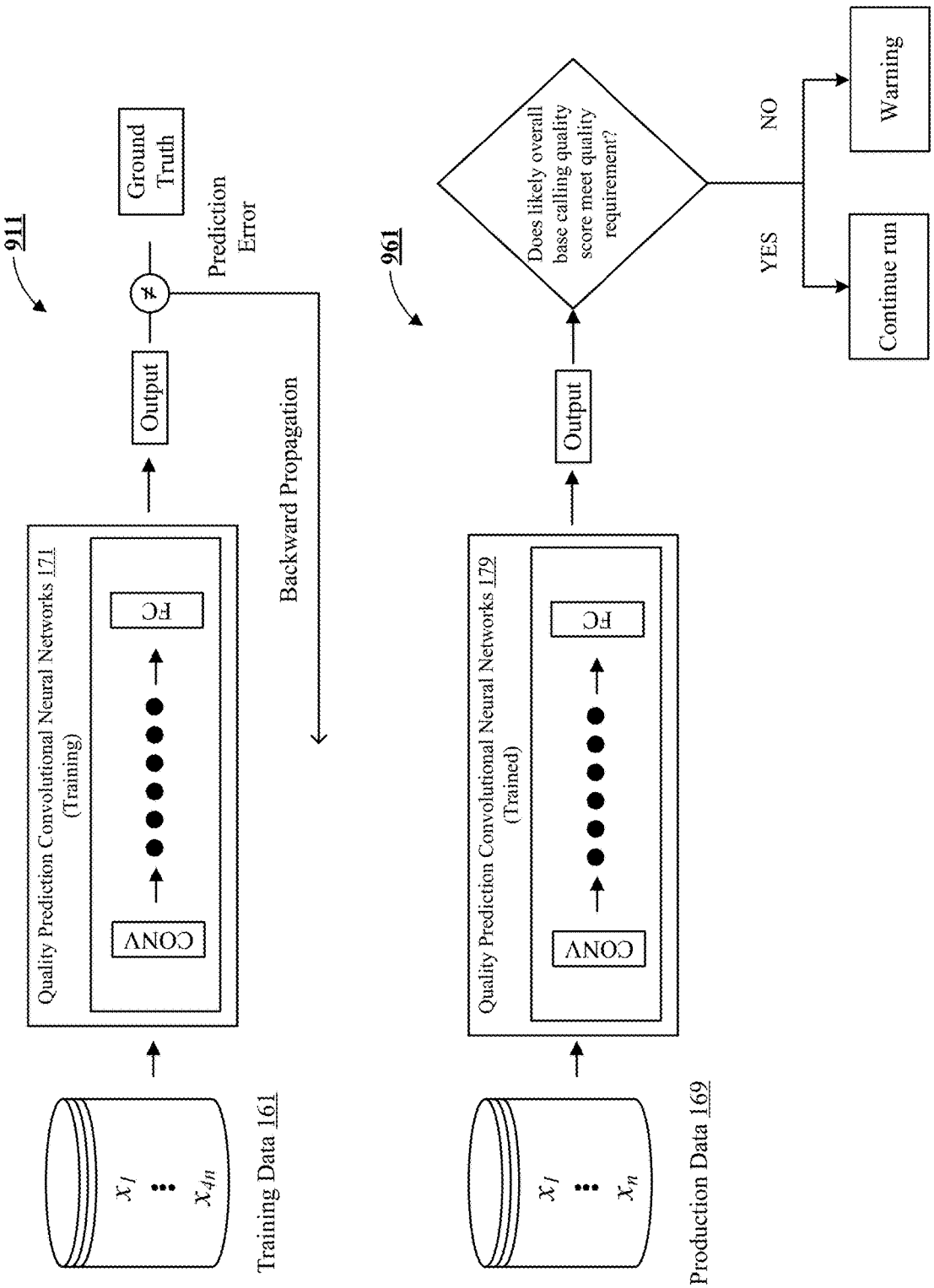
FIG. 9 shows examples of architectural level schematics of quality prediction convolutional neural networks of FIG. 1 in training and production.

FIG. 9 presents schematics 911 and 961 for training and production deployment 900 of the quality prediction convolutional neural networks (CNNs), in accordance with one implementation. During training, the subsystems' performance data and overall base calling quality scores from the training database 161 are given as input to the quality prediction CNNs 171. Each quality prediction CNN contains multiple layers as shown in FIG. 3 for inputs with one channel and in FIG. 4 for inputs with four channels. In one implementation, a different quality prediction CNN is trained for a particular input (i.e., subsystem performance time series and overall base calling quality time series). In another implementation, a single quality prediction CNN is trained for all the inputs. In one implementation, the output of the quality prediction CNN is a likely overall base calling quality for a target cycle in a read of a sequencing run. The output is compared with the ground truth base calling quality for the target cycle. In one implementation, the ground truth is an average base calling quality of ten cycles of a read as discussed above. A prediction error calculated between the output and the ground truth is used to update the weights in quality prediction CNNs so that they cause the output to be closer to the ground truth.

The trained quality prediction CNNs are deployed to a production environment where they receive production data for pre-prediction cycles of reads in sequencing runs of sequencing instruments 111. During production (or inference), the quality prediction CNNs produce likely overall base calling quality scores for target cycles in post-prediction base calling process cycles. The operator 165 can then compare the likely overall base calling quality scores of the read with the required quality of base calls for downstream data analysis. If the likely quality of base calling quality scores for post-prediction cycles is lower than the required quality of base calls, the system warns the operator 165, who can abort the sequencing run.

Computer System

Figure 10:
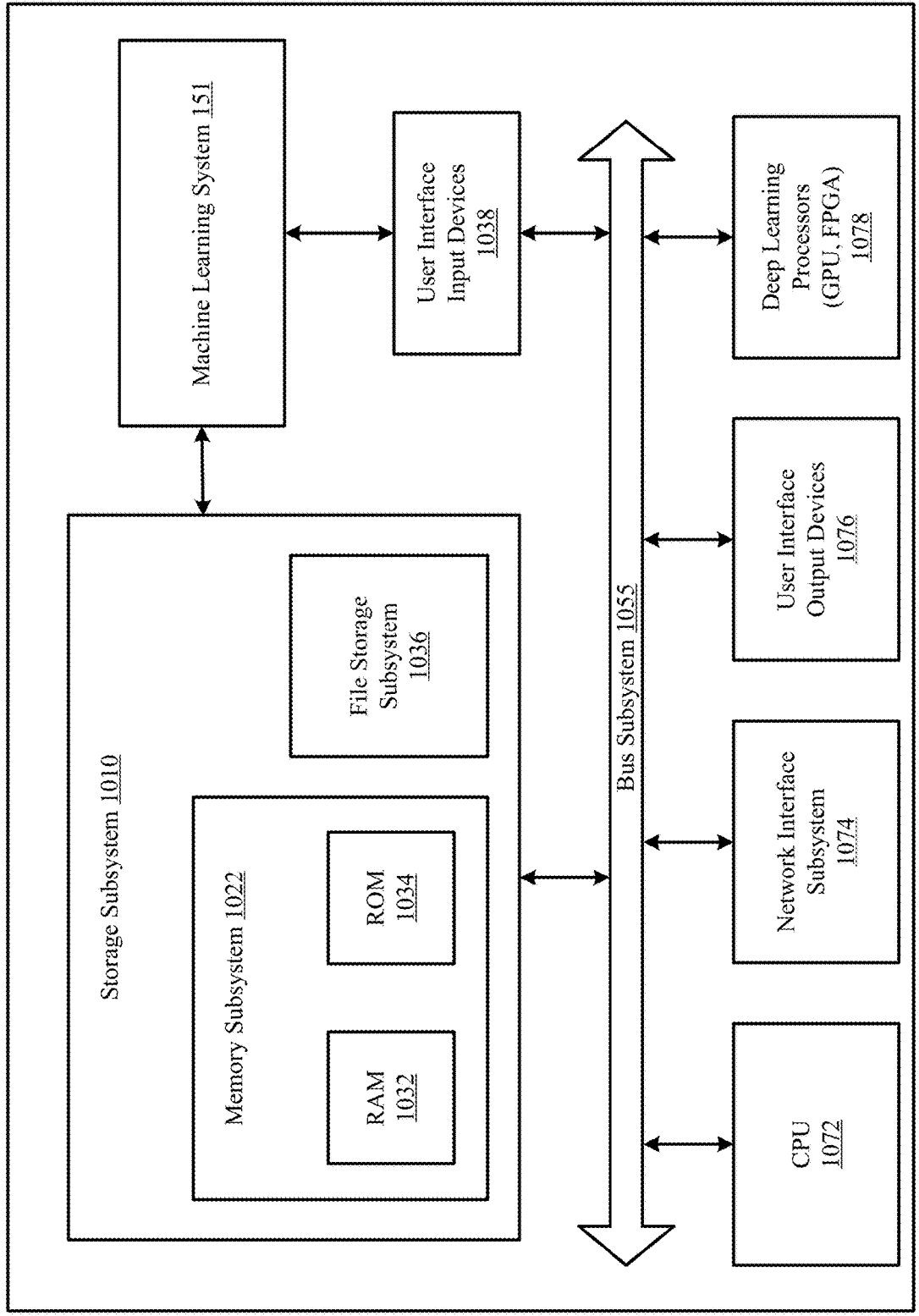
FIG. 10 is a simplified block diagram of a computer system that can be used to implement the machine learning system of FIG. 1.

FIG. 10 is a simplified block diagram of a computer system 1000 that can be used to implement the machine learning system 151 of FIG. 1 for early prediction of base calling quality during an extended optical base calling process. A similar computer system 1000 can implement the machine learning system 159 for production or inference. Computer system 1000 includes at least one central processing unit (CPU) 1072 that communicates with a number of peripheral devices via bus subsystem 1055. These peripheral devices can include a storage subsystem 1010 including, for example, memory devices and a file storage subsystem 1036, user interface input devices 1038, user interface output devices 1076, and a network interface subsystem 1074. The input and output devices allow user interaction with computer system 1000. Network interface subsystem 1074 provides an interface to outside networks, including an interface to corresponding interface devices in other computer systems.

In one implementation, the machine learning system 151 of FIG. 1 is communicably linked to the storage subsystem 1010 and the user interface input devices 1038.

User interface input devices 1038 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 1000.

User interface output devices 1076 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 1000 to the user or to another machine or computer system.

Storage subsystem 1010 stores programming and data constructs that provide the functionality of some or all of the modules and methods described herein. These software modules are generally executed by deep learning processors 1078.

Deep learning processors 1078 can be graphics processing units (GPUs) or field-programmable gate arrays (FPGAs). Deep learning processors 1078 can be hosted by a deep learning cloud platform such as Google Cloud Platform™, Xilinx™, and Cirrascale™. Examples of deep learning processors 1078 include Google's Tensor Processing Unit (TPU)™, rackmount solutions like GX4 Rackmount Series™, GX8 Rackmount Series™, NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, and others.

Memory subsystem 1022 used in the storage subsystem 1010 can include a number of memories including a main random access memory (RAM) 1032 for storage of instructions and data during program execution and a read only memory (ROM) 1034 in which fixed instructions are stored. A file storage subsystem 1036 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 1036 in the storage subsystem 1010, or in other machines accessible by the processor.

Bus subsystem 1055 provides a mechanism for letting the various components and subsystems of computer system 1000 communicate with each other as intended. Although bus subsystem 1055 is shown schematically as a single bus, alternative implementations of the bus subsystem can use multiple busses.

Computer system 1000 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 1000 depicted in FIG. 10 is intended only as a specific example for purposes of illustrating the preferred embodiments of the present invention. Many other configurations of computer system 1000 are possible having more or less components than the computer system depicted in FIG. 10.

Particular Implementations

The technology disclosed relates to early prediction of base calling quality during an extended optical base calling process.

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

A first system implementation of the technology disclosed includes one or more processors coupled to the memory. The memory is loaded with computer instructions to perform early prediction of base calling quality during an extended optical base calling process. The base calling process includes pre-prediction base calling process cycles and at least two times as many post-prediction base calling process cycles as pre-prediction cycles. Each base calling process cycle includes (a) chemical processing to attach an additional complementary nucleotide to a target nucleotide strand at millions of locations on a substrate, (b) camera positioning and image registration over image tiles of the substrate, and (c) image acquisition over the image tiles. The computer instructions, when executed on the processors input a plurality of time series from the pre-prediction base calling process cycles to a trained convolutional neural network. The plurality of time series include chemical processing subsystem performance time series, an image registration subsystem performance time series, an image acquisition subsystem performance time series, and an overall base calling quality time series.

The system trains the convolutional neural network using base calling quality experience comprising the plurality of time series for the pre-prediction base calling process cycles and a post-prediction overall base calling quality time series. The trained convolutional neural network determines, from the pre-prediction base calling process cycles, a likely overall base calling quality expected after at least two times as many post-prediction base calling process cycles as the pre-prediction cycles. Finally, the system outputs the overall base calling quality for operator evaluation.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

The system includes representing the chemical processing performance in the chemical processing subsystem performance time series by estimates of phasing and prephasing errors. The system includes representing the image registration performance in the image registration subsystem performance time series by reports of x and y image offset adjustment after image capture. The system further includes representing the image acquisition performance in the image acquisition subsystem performance time series by reports of focus and contrast. In such implementation, the system includes representing focus by narrowness of full width half maximum of individual clusters in cluster images. In another such implementation of the system, the contrast includes a minimum contrast calculated as the 10th percentile per channel of a column of the image. In another such implementation of the system, the contrast includes a maximum contrast calculated as the 99.5th percentile per channel of a column of the image.

In one implementation of the system, the image acquisition performance further includes image acquisition subsystem performance time series reports of cluster intensity. In such an implementation, the system reports the cluster intensity at a 90th percentile of intensities of imaged clusters. In one implementation of the system, the base calling process includes 2 to 25 times as many post-prediction base calling process cycles as pre-prediction cycles. In one implementation of the system. In one implementation of the system, the base calling process includes 20 to 50 pre-prediction base calling process cycles. In one implementation of the system, the base calling process includes 100 to 500 post-prediction base calling process cycles.

In one implementation, the system determines from the pre-prediction base calling process cycles likely overall base calling quality for at least five intermediate cycle counts during the post-prediction base calling process cycles. Following the determination, the system outputs the intermediate likely overall base calling quality determinations. In one implementation of the system, the overall overall base calling quality is calculated as a Phred quality score. In another implementation of the system, the overall base calling quality is calculated as a Sanger quality score.

A second system implementation of the technology disclosed includes one or more processors coupled to the memory. The memory is loaded with computer instructions to perform early prediction of base calling quality during an extended optical base calling process that includes a sequence of paired reads, each read includes pre-prediction base calling process cycles and at least two times as many post-prediction base calling process cycles as pre-prediction cycles. Each base calling process cycle include (a) chemical processing to attach an additional complementary nucleotide to a target nucleotide strand at millions of locations on a substrate, (b) camera positioning and image registration over image tiles of the substrate, and (c) image acquisition over the image tiles. The system includes giving a plurality of time series from the pre-prediction base calling process cycles of a second read to a trained convolutional neural network. The plurality of time series comprise a chemical processing subsystem performance time series, an image registration subsystem performance time series, an image acquisition subsystem performance time series, and an overall base calling quality time series. The system also includes giving an overall base calling quality time series of a first read to the trained convolutional neural network.

The system includes training the convolutional neural network using base calling quality experience comprising the plurality of time series for the pre-prediction base calling process cycles of the second read, a post-prediction overall base calling quality time series of the second read, and the overall base calling quality time series of the first read. The trained convolutional neural network use the pre-prediction base calling process cycles of the second read and the overall base calling quality time series of the first read to determine a likely overall base calling quality of the second read expected after at least two times as many post-prediction base calling process cycles as the pre-prediction cycles. Finally, the system outputs the likely overall base calling quality of the second read for operator evaluation. In such an implementation of the system, the first read precedes the second read and comprises base calling a sequenced molecule in a forward direction. The second read comprises base calling the sequenced molecules in a reverse direction.

Each of the features discussed in this particular implementation section for the first system implementation apply equally to the second system implementation. As indicated above, all the system features are not repeated here and should be considered repeated by reference.

Other implementations may include a non-transitory computer readable storage medium storing instructions executable by a processor to perform functions of the system described above. Yet another implementation may include a method performing the functions of the system described above.

A first method implementation of the technology disclosed includes early prediction of base calling quality during an extended optical base calling process. The base calling process cycles include pre-prediction base calling process cycles and at least two times as many post-prediction base calling process cycles as pre-prediction cycles. Each base calling process cycle includes (a) chemical processing to attach an additional complementary nucleotide to a target nucleotide strand at millions of locations on a substrate, (b) camera positioning and image registration over image tiles of the substrate, and (c) image acquisition over the image tiles. The method includes giving a plurality of time series from the pre-prediction base calling process cycles to a trained convolutional neural network. The plurality of time series include a chemical processing subsystem performance time series, an image registration subsystem performance time series, an image acquisition subsystem performance time series, and an overall base calling quality time series.

The method further includes training the convolutional neural network using base calling quality experience comprising the plurality of time series for the pre-prediction base calling process cycles and a post-prediction overall base calling quality time series. The trained convolutional neural network determines a likely overall base calling quality expected after at least two times as many post-prediction base calling process cycles as the pre-prediction cycles from the pre-prediction base calling process cycles. Finally, the method outputs the likely overall base calling quality for operator evaluation.

Each of the features discussed in this particular implementation section for the first system implementation apply equally to this method implementation. As indicated above, all the system features are not repeated here and should be considered repeated by reference.

Other implementations may include a non-transitory computer readable storage medium storing instructions executable by a processor to perform the first method described above. Yet another implementation may include a system including memory and one or more processors operable to execute instructions, stored in the memory, to perform the first method described above.

Computer readable media (CRM) implementations of the technology disclosed include a non-transitory computer readable storage medium impressed with computer program instructions, when executed on a processor, implement the method described above.

Each of the features discussed in this particular implementation section for the first system implementation apply equally to the CRM implementation. As indicated above, all the system features are not repeated here and should be considered repeated by reference.

A second method implementation of the technology disclosed includes early prediction of base calling quality during an extended optical base calling process that includes a sequence of paired reads. Each read includes pre-prediction base calling process cycles and at least two times as many post-prediction base calling process cycles as pre-prediction cycles. Each base calling process cycle includes (a) chemical processing to attach an additional complementary nucleotide to a target nucleotide strand at millions of locations on a substrate, (b) camera positioning and image registration over image tiles of the substrate, and (c) image acquisition over the image tiles. The method includes giving a plurality of time series from the pre-prediction base calling process cycles of a second read to a trained convolutional neural network. The plurality of time series comprise a chemical processing subsystem performance time series, an image registration subsystem performance time series, an image acquisition subsystem performance time series, and an overall base calling quality time series. The method also includes giving an overall base calling quality time series of a first read to the trained convolutional neural network.

The method includes training the convolutional neural network using base calling quality experience comprising the plurality of time series for the pre-prediction base calling process cycles of the second read, a post-prediction overall base calling quality time series of the second read, and the overall base calling quality time series of the first read. The trained convolutional neural network use the pre-prediction base calling process cycles of the second read and the overall base calling quality time series of the first read to determine a likely overall base calling quality of the second read expected after at least two times as many post-prediction base calling process cycles as the pre-prediction cycles. Finally, the method outputs the likely overall base calling quality of the second read for operator evaluation. In the second method implementation, the first read precedes the second read and comprises base calling a sequenced molecule in a forward direction. The second read comprises base calling the sequenced molecules in a reverse direction.

Each of the features discussed in this particular implementation section for the first system implementation apply equally to this method implementation. As indicated above, all the system features are not repeated here and should be considered repeated by reference.

Other implementations may include a non-transitory computer readable storage medium storing instructions executable by a processor to perform the method described above. Yet another implementation may include a system including memory and one or more processors operable to execute instructions, stored in the memory, to perform the method described above.

Computer readable media (CRM) implementations of the technology disclosed include a non-transitory computer readable storage medium impressed with computer program instructions, when executed on a processor, implement the second method described above.

Each of the features discussed in this particular implementation section for the first system implementation apply equally to the CRM implementation. As indicated above, all the system features are not repeated here and should be considered repeated by reference.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein. The scope of the technology disclosed is defined by the appended claims.

What is claimed is:

1. A method of early prediction of base calling quality during an extended optical base calling process that includes pre-prediction base calling process cycles and at least two times as many post-prediction base calling process cycles as pre-prediction cycles, wherein each base calling process cycle includes (a) chemical processing to attach an additional complementary nucleotide to a target nucleotide strand at millions of locations on a substrate, (b) camera positioning and image registration over image tiles of the substrate, and (c) image acquisition over the image tiles, the method including:
inputting to a trained convolutional neural network a plurality of time series from the pre-prediction base calling process cycles, the plurality of time series comprising a chemical processing subsystem performance time series, an image registration subsystem performance time series, an image acquisition subsystem performance time series, and an overall base calling quality time series;
wherein the trained convolutional neural network is trained using base calling quality experience comprising the plurality of time series for the pre-prediction base calling process cycles and a post-prediction overall base calling quality time series;
the trained convolutional neural network determining, from the pre-prediction base calling process cycles, a predicted overall base calling quality expected after at least two times as many post-prediction base calling process cycles as the pre-prediction cycles; and
outputting the predicted overall base calling quality for operator evaluation.

2. The method of claim 1, wherein the chemical processing performance is represented in the chemical processing subsystem performance time series by estimates of phasing and prephasing errors.

3. The method of claim 1, wherein the image registration performance is represented in the image registration subsystem performance time series by reports of x and y image offset adjustment after image capture.

4. The method of claim 1, wherein the image acquisition performance is represented in the image acquisition subsystem performance time series by reports of focus and contrast.

5. The method of claim 4, wherein the focus is represented by average width of full width half maximum of individual clusters in cluster images.

6. The method of claim 4, wherein the contrast includes a minimum contrast calculated as the 10th percentile per channel of a column of the image.

7. The method of claim 4, wherein the contrast includes a maximum contrast calculated as the 99.5th percentile per channel of a column of the image.

8. The method of claim 4, wherein the image acquisition performance further includes image acquisition subsystem performance time series reports of cluster intensity.

9. The method of claim 8, wherein the cluster intensity is reported at a 90th percentile of intensities of imaged clusters.

10. The method of claim 1, wherein the base calling process includes 3 to 25 times as many post-prediction base calling process cycles as pre-prediction cycles.

11. The method of claim 1, wherein the base calling process includes 2 to 50 times as many post-prediction base calling process cycles as pre-prediction cycles.

12. The method of claim 1, wherein the base calling process includes 20 to 50 pre-prediction base calling process cycles.

13. The method of claim 1, wherein the base calling process includes 100 to 500 post-prediction base calling process cycles.

14. The method of claim 1, further including determining from the pre-prediction base calling process cycles the predicted overall base calling quality for at least five intermediate cycle counts during the post-prediction base calling process cycles and outputting the intermediate predicted overall base calling quality determinations.

15. A method of early prediction of base calling quality during an extended optical base calling process that includes a sequence of paired reads, each read including pre-prediction base calling process cycles and at least two times as many post-prediction base calling process cycles as pre-prediction cycles, each base calling process cycle including (a) chemical processing to attach an additional complementary nucleotide to a target nucleotide strand at millions of locations on a substrate, (b) camera positioning and image registration over image tiles of the substrate, and (c) image acquisition over the image tiles, the method including:
- inputting to a trained convolutional neural network
  - a plurality of time series from the pre-prediction base calling process cycles of a second read, the plurality of time series comprising a chemical processing subsystem performance time series, an image registration subsystem performance time series, an image acquisition subsystem performance time series, and an overall base calling quality time series, and
  - an overall base calling quality time series of a first read;
- wherein the trained convolutional neural network is trained using base calling quality experience comprising the plurality of time series for the pre-prediction base calling process cycles of the second read, a post-prediction overall base calling quality time series of the second read, and the overall base calling quality time series of the first read;
- the trained convolutional neural network determining, from the pre-prediction base calling process cycles of the second read and the overall base calling quality time series of the first read, a predicted overall base calling quality of the second read expected after at least two times as many post-prediction base calling process cycles as the pre-prediction cycles; and
- outputting the predicted overall base calling quality of the second read for operator evaluation.

16. A system including one or more processors coupled to memory, the memory loaded with computer instructions to perform early prediction of base calling quality during an extended optical base calling process that includes pre-prediction base calling process cycles and at least two times as many post-prediction base calling process cycles as pre-prediction cycles, wherein each base calling process cycle includes (a) chemical processing to attach an additional complementary nucleotide to a target nucleotide strand at millions of locations on a substrate, (b) camera positioning and image registration over image tiles of the substrate, and (c) image acquisition over the image tiles, the instructions, when executed on the processors, implement actions comprising:
- inputting to a trained convolutional neural network a plurality of time series from the pre-prediction base calling process cycles, the plurality of time series comprising a chemical processing subsystem performance time series, an image registration subsystem performance time series, an image acquisition subsystem performance time series, and an overall base calling quality time series;
- wherein the trained convolutional neural network is trained using base calling quality experience comprising the plurality of time series for the pre-prediction base calling process cycles and a post-prediction overall base calling quality time series;
- the trained convolutional neural network determining, from the pre-prediction base calling process cycles, a predicted overall base calling quality expected after at least two times as many post-prediction base calling process cycles as the pre-prediction cycles; and
- outputting the predicted overall base calling quality for operator evaluation.

17. The system of claim 16, wherein the chemical processing performance is represented in the chemical processing subsystem performance time series by estimates of phasing and prephasing errors.

18. A non-transitory, computer-readable medium having computer executable instructions that a method of early prediction of base calling quality during an extended optical base calling process that includes pre-prediction base calling process cycles and at least two times as many post-prediction base calling process cycles as pre-prediction cycles, wherein each base calling process cycle includes (a) chemical processing to attach an additional complementary nucleotide to a target nucleotide strand at millions of locations on a substrate, (b) camera positioning and image registration over image tiles of the substrate, and (c) image acquisition over the image tiles, the method including:
- inputting to a trained convolutional neural network a plurality of time series from the pre-prediction base calling process cycles, the plurality of time series comprising a chemical processing subsystem performance time series, an image registration subsystem performance time series, an image acquisition subsystem performance time series, and an overall base calling quality time series;
- wherein the trained convolutional neural network is trained using base calling quality experience comprising the plurality of time series for the pre-prediction base calling process cycles and a post-prediction overall base calling quality time series;
- the trained convolutional neural network determining, from the pre-prediction base calling process cycles, a predicted overall base calling quality expected after at least two times as many post-prediction base calling process cycles as the pre-prediction cycles; and
- outputting the predicted overall base calling quality for operator evaluation.

19. A computer system running on numerous parallel processors adapted to perform a method of early prediction of base calling quality during an extended optical base calling process that includes a sequence of paired reads, each read including pre-prediction base calling process cycles and at least two times as many post-prediction base calling process cycles as pre-prediction cycles, each base calling process cycle including (a) chemical processing to attach an additional complementary nucleotide to a target nucleotide strand at millions of locations on a substrate, (b) camera positioning and image registration over image tiles of the substrate, and (c) image acquisition over the image tiles, the method including:
- inputting to a trained convolutional neural network
  - a plurality of time series from the pre-prediction base calling process cycles of a second read, the plurality of time series comprising a chemical processing subsystem performance time series, an image registration subsystem performance time series, an image acquisition subsystem performance time series, and an overall base calling quality time series, and
  - an overall base calling quality time series of a first read;
- wherein the trained convolutional neural network is trained using base calling quality experience comprising the plurality of time series for the pre-prediction base calling process cycles of the second read, a post-prediction overall base calling quality time series of the second read, and the overall base calling quality time series of the first read;

the trained convolutional neural network determining, from the pre-prediction base calling process cycles of the second read and the overall base calling quality time series of the first read, a predicted overall base calling quality of the second read expected after at least two times as many post-prediction base calling process cycles as the pre-prediction cycles; and outputting the predicted overall base calling quality of the second read for operator evaluation.

20. A non-transitory, computer-readable medium having computer executable instructions that implement a method of early prediction of base calling quality during an extended optical base calling process that includes a sequence of paired reads, each read including pre-prediction base calling process cycles and at least two times as many post-prediction base calling process cycles as pre-prediction cycles, each base calling process cycle including (a) chemical processing to attach an additional complementary nucleotide to a target nucleotide strand at millions of locations on a substrate, (b) camera positioning and image registration over image tiles of the substrate, and (c) image acquisition over the image tiles, the method including:

inputting to a trained convolutional neural network
    a plurality of time series from the pre-prediction base calling process cycles of a second read, the plurality of time series comprising a chemical processing subsystem performance time series, an image registration subsystem performance time series, an image acquisition subsystem performance time series, and an overall base calling quality time series, and
    an overall base calling quality time series of a first read;
wherein the trained convolutional neural network is trained using base calling quality experience comprising the plurality of time series for the pre-prediction base calling process cycles of the second read, a post-prediction overall base calling quality time series of the second read, and the overall base calling quality time series of the first read;
the trained convolutional neural network determining, from the pre-prediction base calling process cycles of the second read and the overall base calling quality time series of the first read, a predicted overall base calling quality of the second read expected after at least two times as many post-prediction base calling process cycles as the pre-prediction cycles; and
outputting the predicted overall base calling quality of the second read for operator evaluation.

\* \* \* \* \*